(12) United States Patent
Reid

(10) Patent No.: US 6,844,016 B2
(45) Date of Patent: Jan. 18, 2005

(54) RAPID METHOD FOR PREDICTING TOMATO PASTE CONSISTENCY

(75) Inventor: David S. Reid, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/641,775

(22) Filed: Aug. 14, 2003

(65) Prior Publication Data

US 2004/0101600 A1 May 27, 2004

Related U.S. Application Data

(60) Provisional application No. 60/403,793, filed on Aug. 14, 2002.

(51) Int. Cl.$^7$ .................................................. A23L 1/00
(52) U.S. Cl. ........................ 426/231; 426/524; 426/615
(58) Field of Search ................................ 426/231, 524, 426/615, 665

(56) References Cited

U.S. PATENT DOCUMENTS 4,437,934 A * 3/1984 Nelson et al. ............... 426/231
5,524,451 A * 6/1996 Tippmann .................... 62/352

OTHER PUBLICATIONS

Alviar, Maria; "The influence of serum constituents on the physico–chemical characteristics of pectins and lomato juice model systems during concentration"; *Dissertation: University of California Davis*; 1990.

Kotte, Karsten; "Influence of polymers and water on the functional properties of foods"; *Dissertation: University of California Davis*; 2000; UMI Dissertation Services; Ann Arbor, Michigan, USA.

* cited by examiner

*Primary Examiner*—George C. Yeung
(74) *Attorney, Agent, or Firm*—Townsend and Townsend and Crew LLP

(57) ABSTRACT

The present invention provides a method for predicting tomato paste consistency loss and yield loss.

13 Claims, 23 Drawing Sheets

| Variety ID | Apparent viscosity at 50s$^{-1}$, (mPa.s) | | | | Apparent viscosity at 100$^{-1}$, (mPa.s) | | | |
|---|---|---|---|---|---|---|---|---|
| | Control Juice | 30°Brix Paste | -5°C Frozen Juice | -8°C Frozen Juice | Control Juice | 30°Brix Paste | -5°C Frozen Juice | -8°C Frozen Juice |
| 15 | 190 | 50.6 | 93.7 | 98.4 | 130.8 | 32.5 | 57.5 | 65.4 |
| 30 | 374.7 | 82.5 | 130.4 | 137.5 | 247.0 | 50.4 | 81.6 | 89.0 |
| 31 | 232.7 | 47.1 | 133.3 | 131.5 | 157.2 | 32.5 | 84.2 | 88.2 |
| 34 | 198.8 | 23.3 | 69.6 | 94.7 | 134.7 | 15.9 | 45.9 | 66.0 |

Figure 1

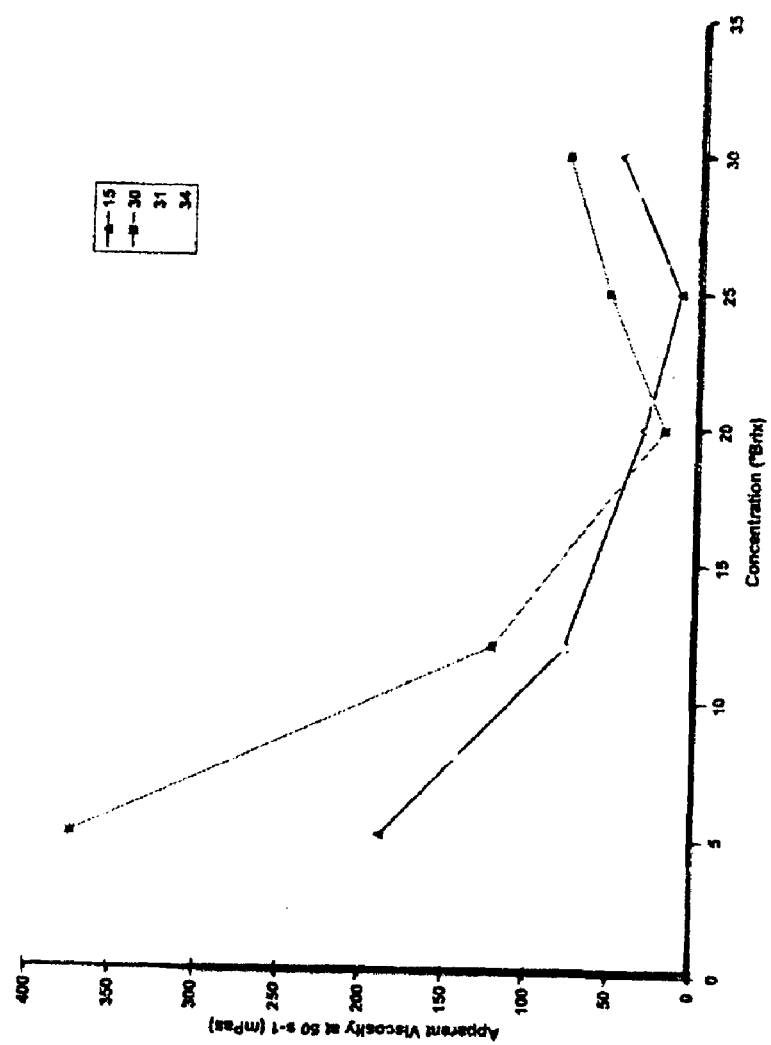

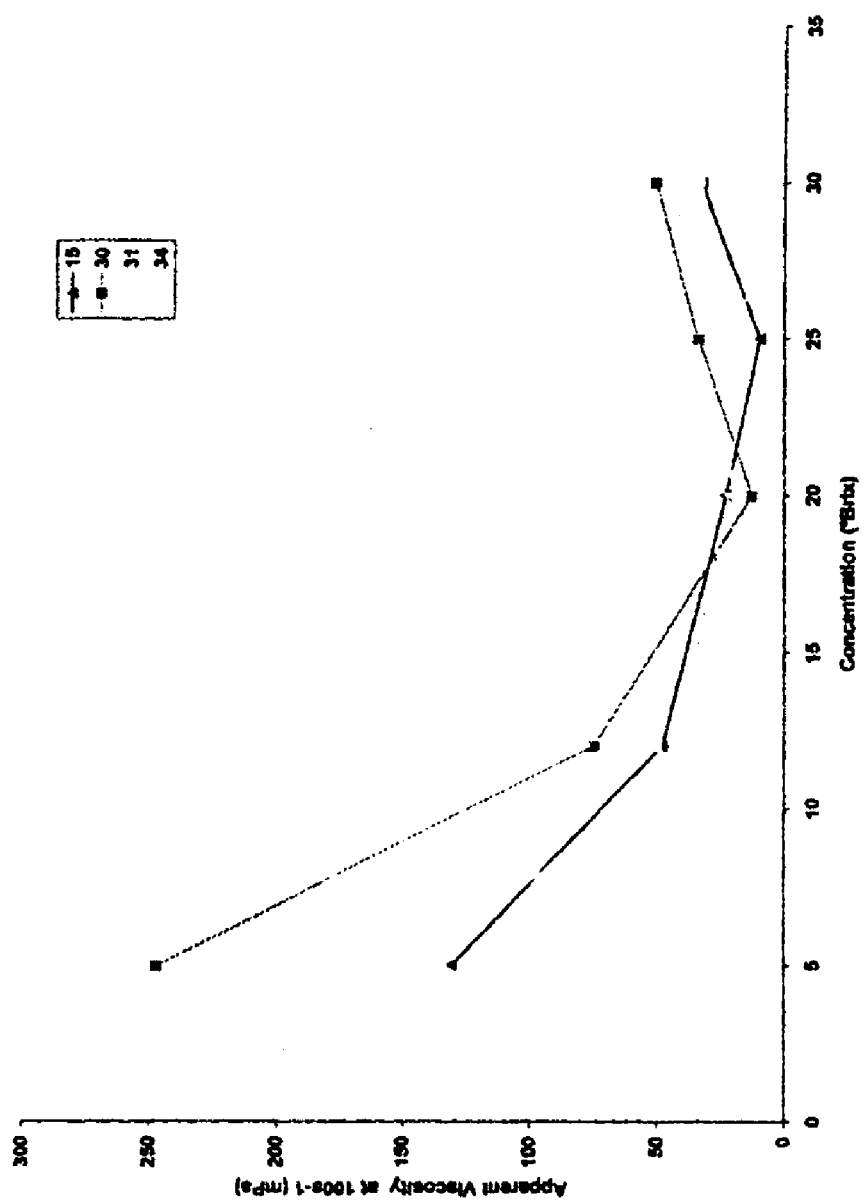

| Variety ID | Apparent viscosity at 50s⁻¹, (mPa.s) | | | | Apparent viscosity at 100s⁻¹, (mPa.s) | | | |
|---|---|---|---|---|---|---|---|---|
| | Control Juice[a] | 30°Brix Paste[a] | -5°C Frozen Juice[b] | -8°C Frozen Juice[b] | Control Juice[a] | 30°Brix Paste[a] | -5°C Frozen Juice[b] | -8°C Frozen Juice[b] |
| 15 | 190 ± 14 | 51 ± 8 | 94 ± 13 | 98 ± 10 | 131 ± 6 | 33 ± 4 | 58 ± 9 | 65 ± 6 |
| 30 | 375 ± 18 | 83 ± 31 | 130 ± 14 | 138 ± 12 | 247 ± 11 | 50 ± 17 | 82 ± 7 | 89 ± 6 |
| 31 | 233 ± 27 | 47 ± 7 | 133 ± 24 | 132 ± 13 | 157 ± 16 | 33 ± 4 | 84 ± 16 | 88 ± 12 |
| 34 | 199 ± 6.4 | 23 ± 2 | 70 ± 14 | 95 ± 11 | 135 ± 5 | 16 ± 2 | 46 ± 2 | 66 ± 8 |

[a] Mean ± standard deviation; n = 4
[b] Mean ± standard deviation; n = 12

Figure 8

| Variety ID | Apparent viscosity at 50s-1, (mPa.s) | | | | Apparent viscosity at 100-1, (mPa.s) | | | |
|---|---|---|---|---|---|---|---|---|
| | -5°C Frozen Juice | | -8°C Frozen Juice | | 5°C Frozen Juice | | -8°C Frozen Juice | |
| | (1 month) | (6 months) | (1 month) | (6 months) | (1 month) | (6 months) | (1 month) | (6 months) |
| 15 | 93.7 | 96.6 | 98.4 | 96.3 | 57.5 | 59.6 | 65.4 | 60.6 |
| 30 | 130.4 | 128.5 | 137.5 | 141.5 | 81.6 | 81.4 | 89.0 | 89.8 |
| 31 | 133.3 | 126.7 | 131.5 | 130.5 | 84.2 | 77.0 | 88.2 | 81.8 |
| 34 | 69.6 | 69.8 | 94.7 | 91.4 | 45.9 | 45.8 | 66.0 | 61.3 |

Figure 9

| Variety ID | Apparent viscosity at 50s⁻¹, (mPa.s) | | | | Apparent viscosity at 100s⁻¹, (mPa.s) | | | |
|---|---|---|---|---|---|---|---|---|
| | Control Juice | 30°Brix Paste | -5°C Frozen Juice | -8°C Frozen Juice | Control Juice | 30°Brix Paste | -5°C Frozen Juice | -8°C Frozen Juice |
| 5557 | 200.1 | 84.9 | 122.4 | 175.9 | 133.3 | 51.2 | 83.4 | 123.1 |
| 5558 | 169.5 | 101.3 | 157.2 | 157.4 | 108.3 | 63.8 | 103.3 | 104.7 |
| 5559 | 190.0 | 101.7 | 130.3 | 150.1 | 129.5 | 61.2 | 87.4 | 99.6 |
| 5560 | 309.1 | 151.6 | 196.5 | 218.3 | 207.2 | 100.2 | 126.5 | 146.8 |
| 5561 | 199.5 | 91.5 | 123.4 | 140.8 | 136.9 | 53.3 | 84.5 | 95.9 |
| 5562 | 248.2 | 145.0 | 171.6 | 177.2 | 169.4 | 88.6 | 114.2 | 116.9 |
| 5563 | 155.7 | 77.2 | 127.3 | 131.6 | 110.1 | 51.0 | 87.5 | 90.1 |
| 5564 | 138.5 | 70.1 | 73.0 | 77.4 | 103.1 | 50.4 | 54.2 | 56.0 |
| 5565 | 227.8 | 96.8 | 146.9 | 208.1 | 153.0 | 61.6 | 95.6 | 132.7 |
| 5566 | 321.8 | 108.6 | 252.2 | 282.5 | 217.6 | 63.6 | 164.2 | 189.0 |
| 5567 | 330.5 | 119.2 | 153.1 | 185.6 | 226.2 | 79.6 | 103.5 | 129.7 |
| 5568 | 137.0 | 77.2 | 86.0 | 92.4 | 94.7 | 53.2 | 58.1 | 62.7 |
| 5569 | 322.7 | 136.4 | 185.4 | 202.3 | 219.6 | 93.7 | 122.8 | 137.7 |

Figure 14A

| Variety ID | Apparent viscosity at 50s-1, (mPa.s) | | | | Control Juice | Apparent viscosity at 100-1, (mPa.s) | | | |
|---|---|---|---|---|---|---|---|---|---|
| | Control Juice | 30°Brix Paste | -5°C Frozen Juice | -8°C Frozen Juice | | 30°Brix Paste | -5°C Frozen Juice | -8°C Frozen Juice | |
| 5570 | 258.7 | 114.4 | 139.6 | 193.6 | 173.1 | 72.1 | 83.4 | 126.5 |
| 5571 | 125.4 | 55.9 | 69.2 | 73.6 | 81.6 | 36.2 | 45.7 | 47.0 |
| 5572 | 83.8 | 37.1 | 44.0 | 50.5 | 49.1 | 27.3 | 26.9 | 31.1 |
| 5573 | 294.0 | 114.6 | 216.4 | 223.0 | 197.5 | 66.5 | 140.5 | 139.6 |
| 5574 | 208.7 | 62.5 | 108.6 | 129.1 | 148.9 | 39.4 | 75.6 | 89.5 |
| 5575 | 214.0 | 148.8 | 159.4 | 161.0 | 138.6 | 86.9 | 101.4 | 102.7 |
| 5577 | 223.8 | 126.2 | 142.5 | 176.6 | 145.7 | 78.8 | 88.9 | 109.0 |
| 5578 | 231.7 | 162.7 | 171.3 | 188.6 | 157.3 | 104.5 | 113.1 | 123.2 |
| 5579 | 299.5 | 161.2 | 173.3 | 173.0 | 205.5 | 103.4 | 120.6 | 115.1 |
| 5580 | 179.2 | 79.8 | 90.8 | 92.8 | 122.7 | 52.2 | 60.0 | 63.3 |
| 5581 | 302.0 | 120.2 | 171.2 | 194.1 | 207.3 | 75.4 | 115.9 | 125.9 |
| 5582 | 242.1 | 111.6 | 154.4 | 173.2 | 166.5 | 66.4 | 101.2 | 107.5 |

Figure 14B

| Variety ID | Apparent viscosity Loss at 50s⁻¹, (mPa.s) | | | Apparent viscosity Loss at 100 s⁻¹, (mPa.s) | | |
|---|---|---|---|---|---|---|
| | 30°Brix Paste | -5°C Frozen Juice | -8°C Frozen Juice | 30°Brix Paste | -5°C Frozen Juice | -8°C Frozen Juice |
| 5557 | 115.2 | 117.7 | 80.5 | 82.0 | 78.4 | 49.8 |
| 5558 | 68.2 | 50.1 | 67.0 | 44.5 | 32.6 | 43.7 |
| 5559 | 88.3 | 99.1 | 96.1 | 68.3 | 70.4 | 70.0 |
| 5560 | 157.5 | 148.5 | 147.2 | 106.9 | 107.2 | 99.4 |
| 5561 | 108.0 | 115.9 | 115.0 | 83.7 | 80.8 | 81.2 |
| 5562 | 103.2 | 113.8 | 127.3 | 80.8 | 82.3 | 92.2 |
| 5563 | 78.5 | 68.0 | 80.3 | 59.1 | 50.8 | 60.3 |
| 5564 | 68.4 | 108.1 | 117.2 | 52.7 | 78.6 | 88.3 |
| 5565 | 131.0 | 119.5 | 76.0 | 91.4 | 85.3 | 59.6 |
| 5566 | 213.3 | 102.6 | 95.8 | 153.9 | 78.2 | 66.6 |
| 5567 | 211.3 | 215.7 | 201.1 | 146.6 | 150.3 | 135.9 |
| 5568 | 59.7 | 92.8 | 100.7 | 41.5 | 66.2 | 73.0 |
| 5569 | 186.3 | 173.8 | 176.7 | 125.9 | 123.4 | 121.1 |

Figure 15A

| Variety ID | Apparent viscosity loss at 50s⁻¹, (mPa.s) | | | Apparent viscosity Loss at 100 s⁻¹, (mPa.s) | | |
|---|---|---|---|---|---|---|
| | 30°Brix Paste | -5°C Frozen Juice | -8°C Frozen Juice | 30°Brix Paste | -5°C Frozen Juice | -8°C Frozen Juice |
| 5570 | 144.3 | 158.0 | 121.4 | 101.0 | 118.1 | 86.1 |
| 5571 | 69.6 | 98.9 | 108.0 | 45.4 | 66.1 | 76.1 |
| 5572 | 46.7 | 83.8 | 89.3 | 21.8 | 53.2 | 59.7 |
| 5573 | 179.4 | 112.5 | 127.3 | 131.0 | 82.9 | 97.1 |
| 5574 | 146.2 | 140.7 | 135.7 | 109.5 | 102.1 | 99.9 |
| 5575 | 65.2 | 92.5 | 109.2 | 51.7 | 64.8 | 75.9 |
| 5577 | 97.6 | 120.1 | 103.5 | 66.9 | 85.0 | 76.6 |
| 5578 | 69.0 | 97.6 | 99.3 | 52.8 | 71.3 | 73.7 |
| 5579 | 138.3 | 163.2 | 182.4 | 102.1 | 111.7 | 130.2 |
| 5580 | 99.5 | 130.0 | 142.5 | 70.4 | 92.1 | 100.4 |
| 5581 | 181.9 | 168.1 | 164.2 | 131.9 | 118.4 | 120.9 |
| 5582 | 130.4 | 125.9 | 125.1 | 100.1 | 92.9 | 98.9 |

RAPID METHOD FOR PREDICTING TOMATO PASTE CONSISTENCY

CROSS-REFERENCES TO RELATED APPLICATIONS

This application claims the benefit of U.S. patent application Ser. No. 60/403,793, filed Aug. 14, 2002, the disclosure of which is hereby incorporated by reference in its entirety for all purposes.

STATEMENT AS TO RIGHTS TO INVENTIONS MADE UNDER FEDERALLY SPONSORED RESEARCH OR DEVELOPMENT

Not applicable.

BACKGROUND OF THE INVENTION

Many fruit and vegetable food products are made by reconstituting or diluting fruit and vegetable pastes. These pastes are typically made from fruit or vegetable purees. There is frequently yield loss associated with the concentration or reduction of the fruit or vegetable purees to pastes prior to their utilization in the manufacture of a desired product. Predicting the yield loss (i.e., screening) provides an important measurement of the amount of starting material required to make a final product of a particular consistency.

Current methods for predicting yield loss in fruit and vegetable pastes tend to be time-consuming and require a large quantity of starting material. Often, the fruit or vegetable paste must actually be made to determine the yield loss. Making the paste requires a large quantity of fruit or vegetable starting material and is time consuming. Pilot Scale screening methods are typically used to predict yield loss. In the case of tomatoes, Pilot Scale screening methods may require as much as two hundred pounds of starting material to produce a sample paste. In addition, the production of the sample paste requires a significant amount of time, i.e., at least three hours per paste. Other methods which require less starting material have been developed. For example, the Bench Scale screening method requires only ten to fifteen pounds of starting material to produce the paste (see, e.g., Karsten Kotte, Influence of polymers and water on the functional properties of foods (2000) (unpublished Ph.D. dissertation, University of California, Davis) (on file with University of California, Davis library) and Maria Salome B. Alviar, The influence of serum constituents on the physico-chemical characteristics of pectins and tomato juice model systems during concentration (1990) (unpublished Ph.D. dissertation, University of California, Davis) (on file with University of California, Davis library). Thus, even for the Bench Scale screening method, the amount of starting material and time required to screen a large number of fruit or vegetable samples is still substantial.

Thus, there is a continuing need in the art for more rapid and efficient screening methods for predicting the amount of yield loss of a fruit or vegetable paste. In particular, a method of screening that does not require the actual production of a fruit or vegetable paste is needed.

BRIEF SUMMARY OF THE INVENTION

The present invention provides a rapid and efficient method for predicting the amount of yield loss of a fruit or vegetable paste.

One embodiment of the present invention provides a method for predicting the yield loss for a fruit or vegetable paste. The fruit or vegetable puree is frozen at about $-4°$ C. to about $-20°$ C. The puree is then thawed and the viscosity of the thawed puree is measured. The viscosity of the thawed puree is compared with viscosity of original puree. In some embodiments, the fruit is a tomato. In some embodiments, the puree is frozen at about $-6°$ C. to about $-12°$ C. In other embodiments, the puree is frozen at about $-8°$ C. In even other embodiments, the puree is frozen for at least 24, 48, or 72 hours before the step of thawing. In yet other embodiments, the viscosity is measured using a consistometer.

Another embodiment of the present invention provides a method for predicting the yield loss for a tomato paste. The tomato puree is frozen at about $-8°$ C. The puree is then thawed and the viscosity of the thawed puree is measured. The viscosity of the thawed puree is compared with viscosity of original puree. In some embodiments, the tomato puree is frozen for at least 24, 48, or 72 hours before the step of thawing. In other embodiments, the viscosity is measured using a consistometer.

These and other embodiments and advantages of the present invention will be apparent from the detailed description that follows.

BRIEF DESCRIPTION OF THE DRAWINGS

FIG. 1 shows data representing measurements of Reconstituted 30° Brix Paste vs. Thawed Pseudo-concentrated Juice Apparent viscosity (mPa.s)

FIG. 8 shows data representing measurements of 30° Brix Paste vs. Frozen Juice Apparent viscosity (mPa.s).

FIG. 9 shows data representing measurements of effect of Storage Time on Thawed Pseudo-concentrated Juice Apparent Viscosity at 50 and 100 $s^{-1}$

FIGS. 14A and 14B shows data representing measurements of reconstituted 30° Brix Paste vs Thawed −5 and −8° C. Pseudo-concentrated Juice Apparent Viscosity 50 and 100 s$^{-1}$.

FIGS. 15A and 15B show data representing prediction of Apparent Viscosity Loss for Reconstituted 30° Brix Paste, Thawed −5 and −8° C. Pseudo-concentrated Juice at 50 and 100 s$^{-1}$.

DETAILED DESCRIPTION OF THE INVENTION

I. Introduction

Figure 2:
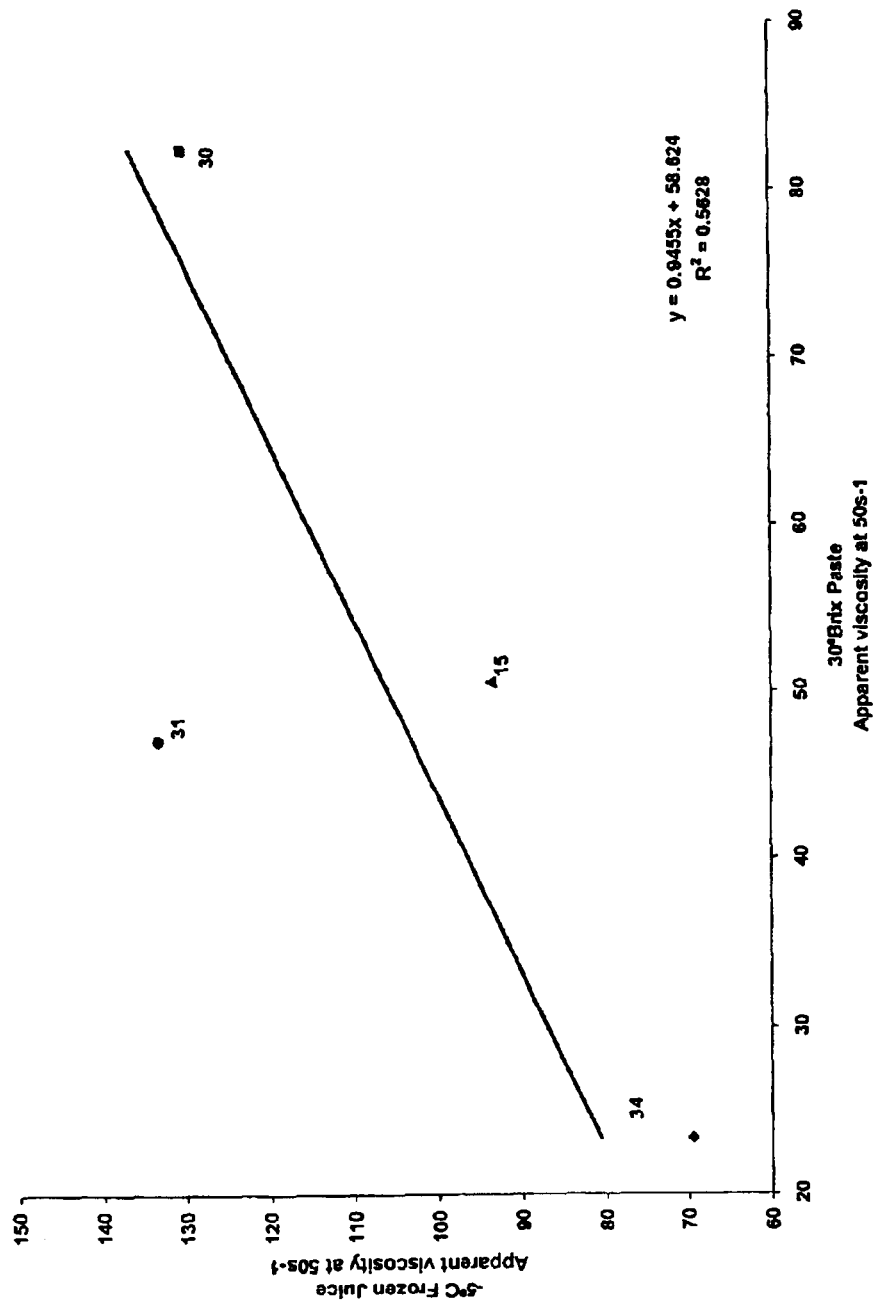
FIG. 2 illustrates data showing apparent viscosity at a shear rate of 50 $s^{-1}$ ($\eta_{50}$) of concentrates diluted to original ° Brix versus apparent viscosity of $-5°$ C. pseudo-concentrated juices.
Figure 3:
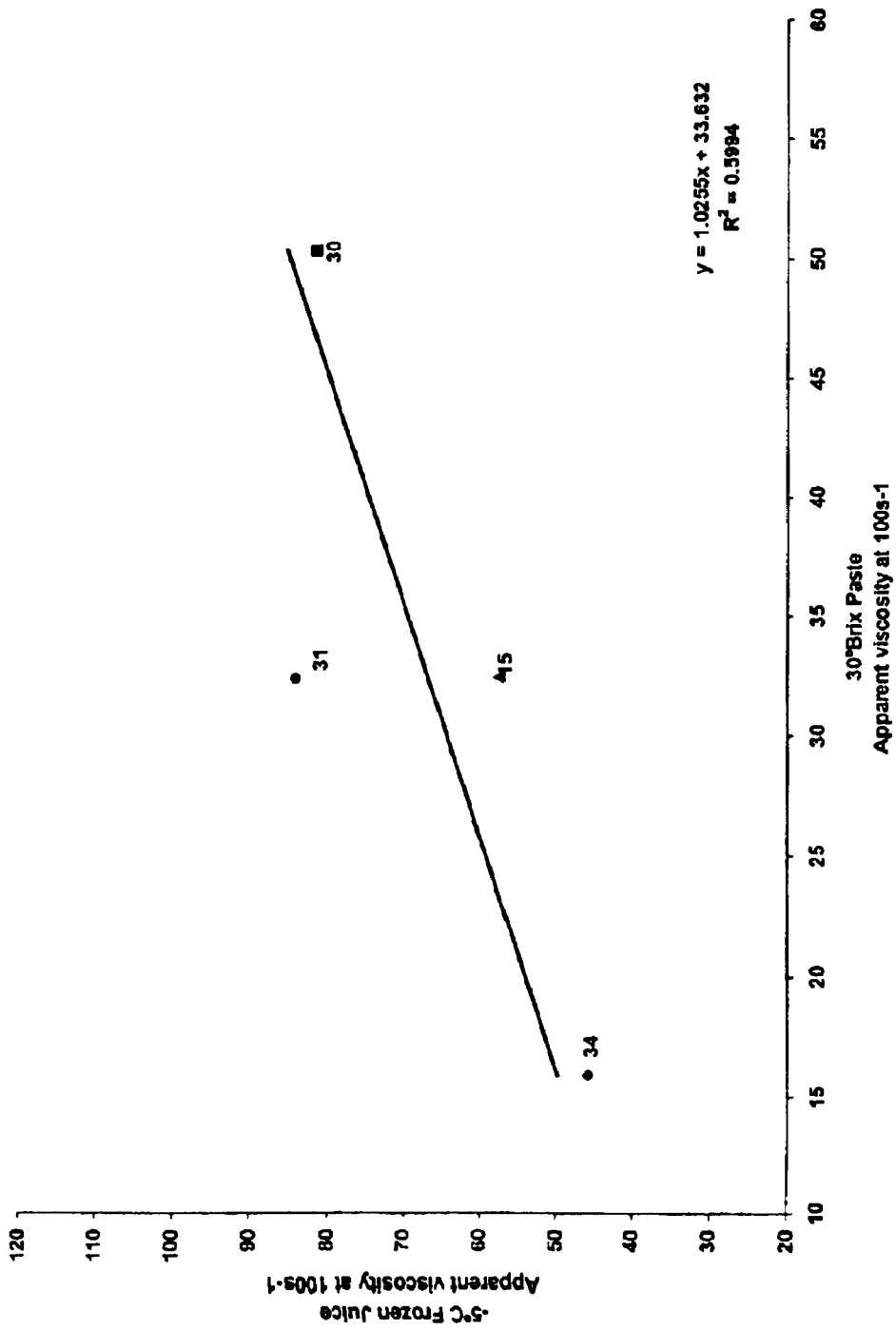
FIG. 3 illustrates data showing apparent viscosity at a shear rate of 100 $s^{-1}$ ($\eta_{100}$) of concentrates diluted to original ° Brix versus apparent viscosity of $-5°$ C. pseudo-concentrated juices.
Figure 4:
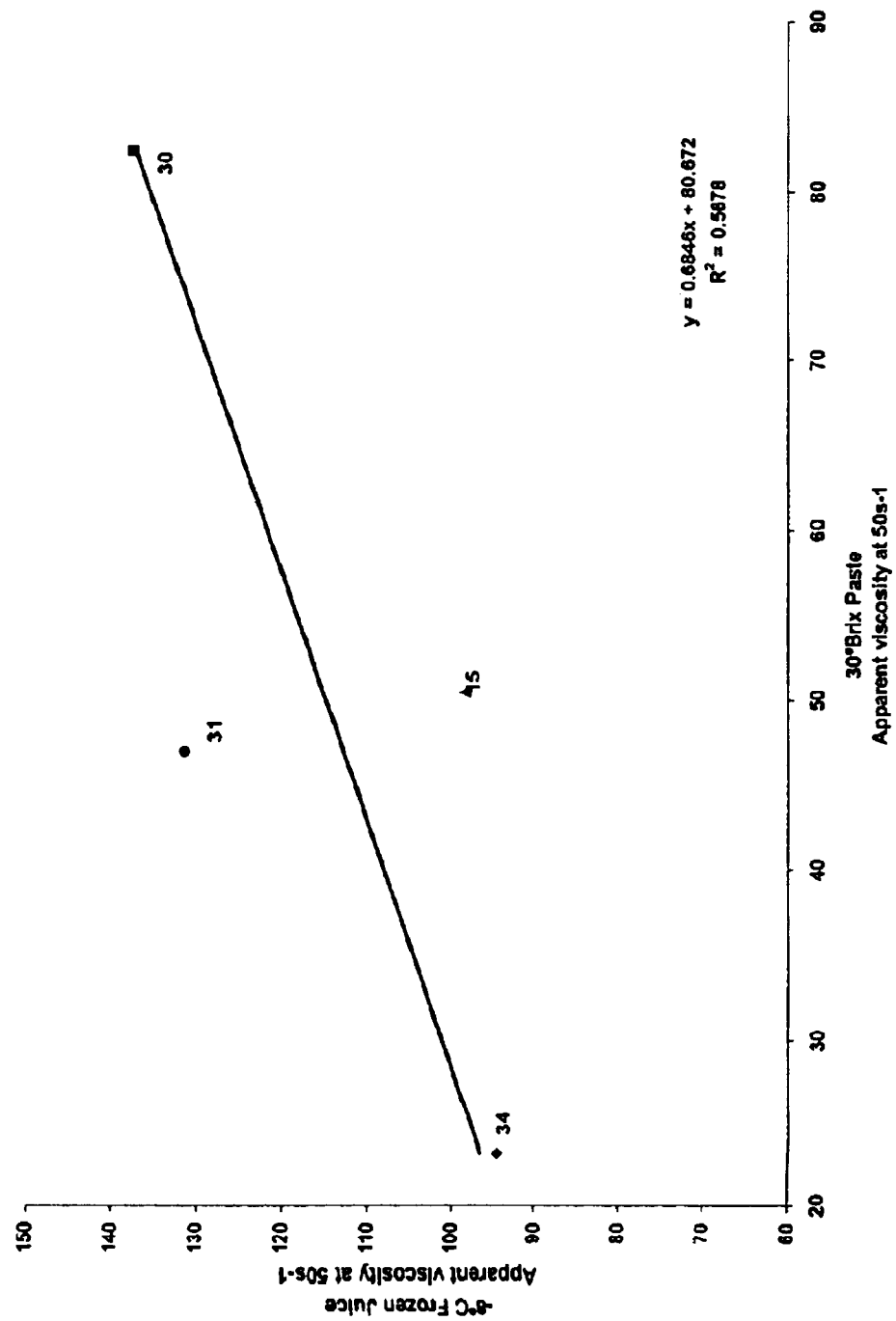
FIG. 4 illustrates data showing apparent viscosity at a shear rate of 50 $s^{-1}$ ($\eta_{50}$) of concentrates diluted to original ° Brix versus apparent viscosity of $-8°$ C. pseudo-concentrated juices.
Figure 5:
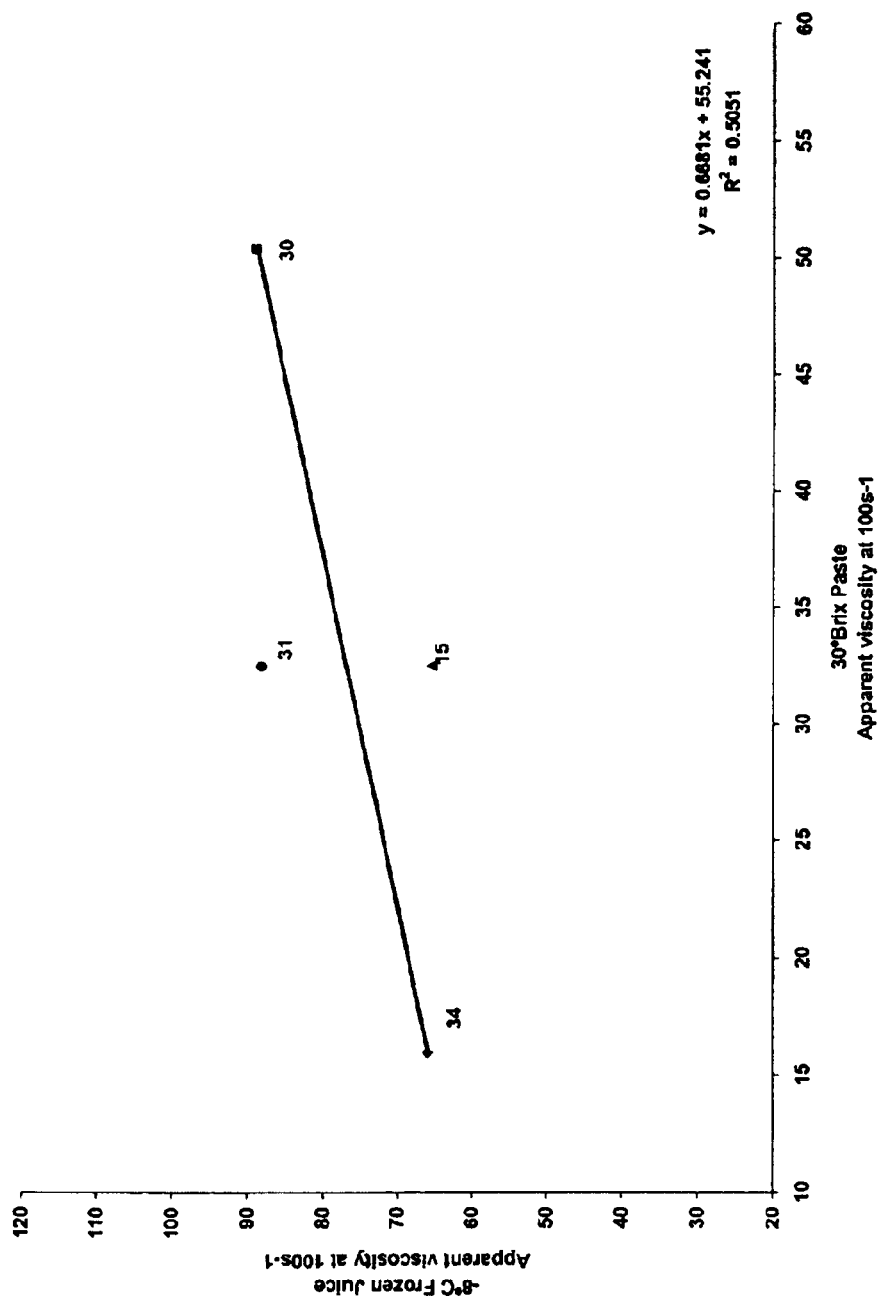
FIG. 5 illustrates data showing apparent viscosity at a shear rate of 100 $s^{-1}$ ($\eta_{100}$) of concentrates diluted to original ° Brix versus apparent viscosity of $-8°$ C. pseudo-concentrated juices.
Figure 10:
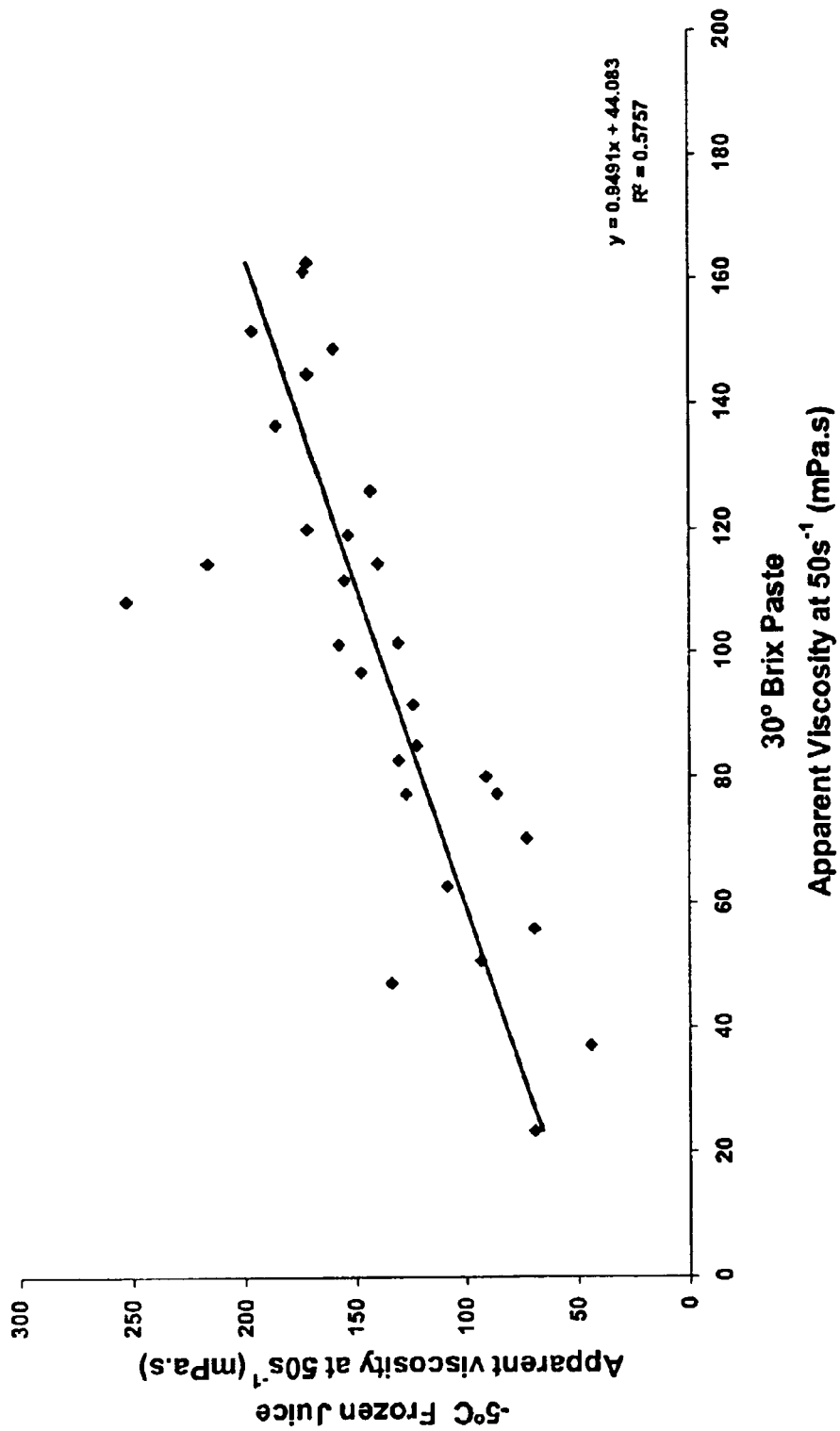
FIG. 10 illustrates data showing apparent viscosity at shear rate 50 $s^{-1}$ of 30° Brix concentrates diluted to original ° Brix versus apparent viscosity of $-5°$ C. pseudo-concentrated juices.
Figure 11:
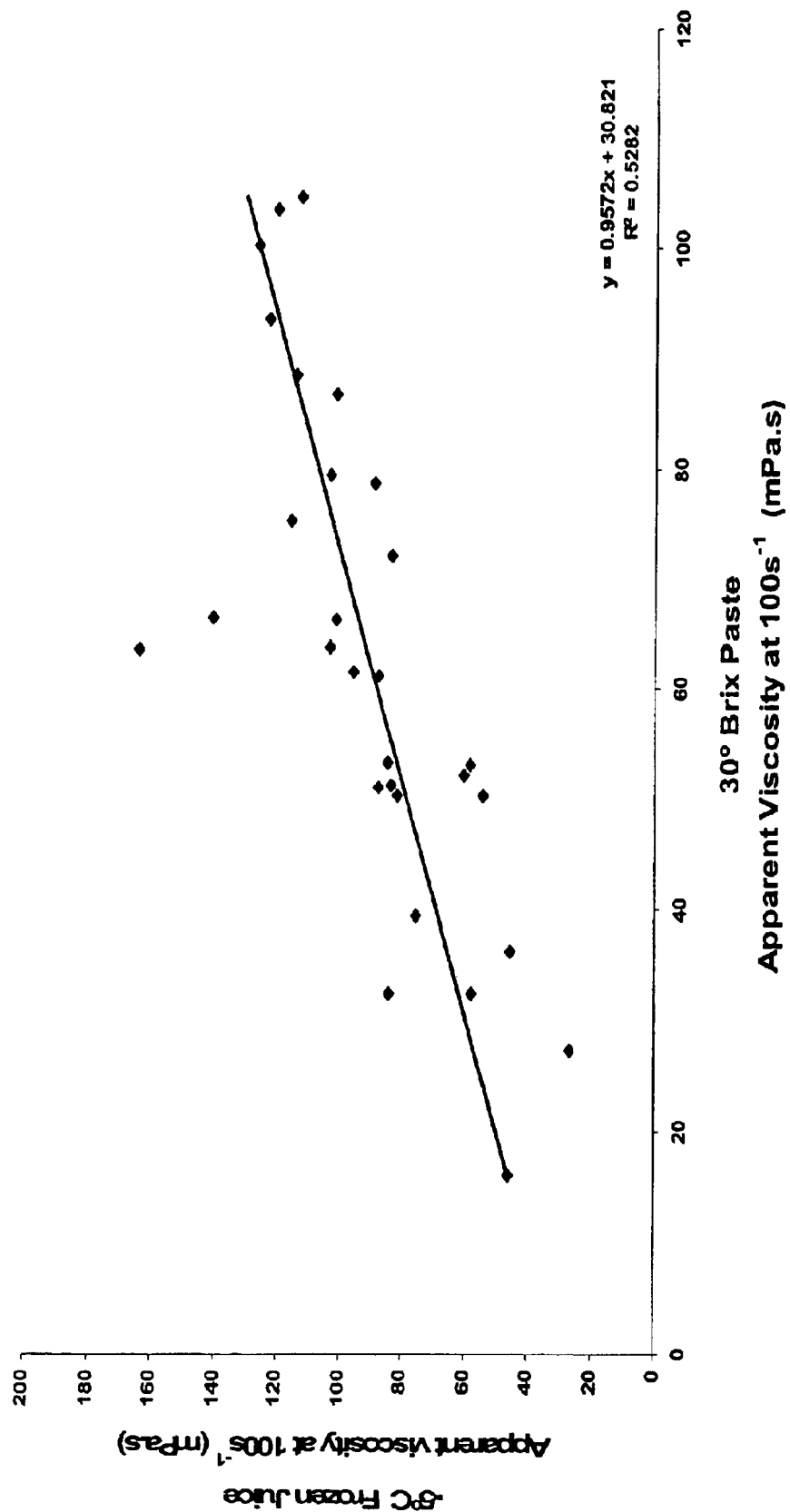
FIG. 11 illustrates data showing apparent viscosity at shear rate 100 $s^{-1}$ of 30° Brix concentrates diluted to original ° Brix versus apparent viscosity of $-5°$ C. pseudo-concentrated juices.
Figure 12:
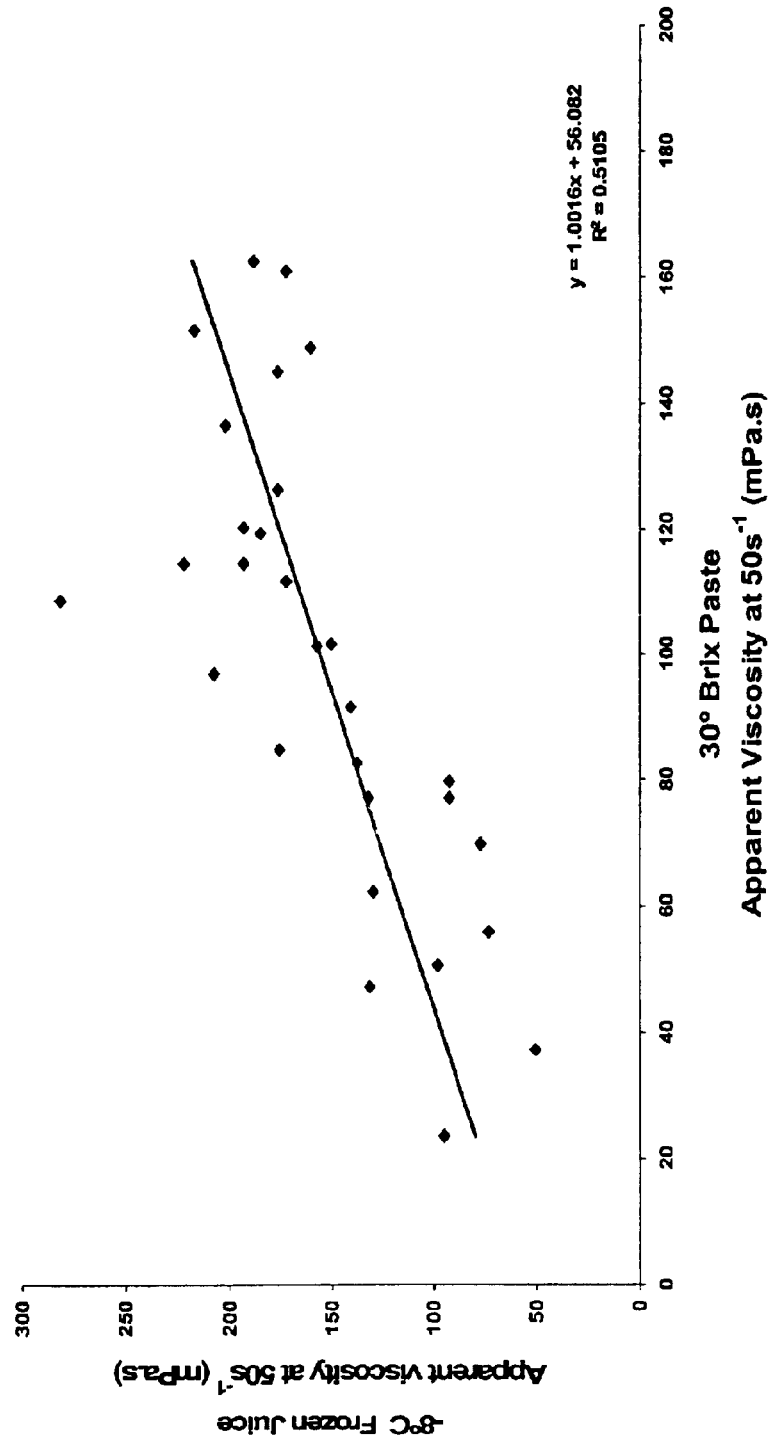
FIG. 12 illustrates data showing apparent viscosity at shear rate 50 $s^{-1}$ of 30° Brix concentrates diluted to original ° Brix versus apparent viscosity of −8° C. pseudo-concentrated juices.
Figure 13:
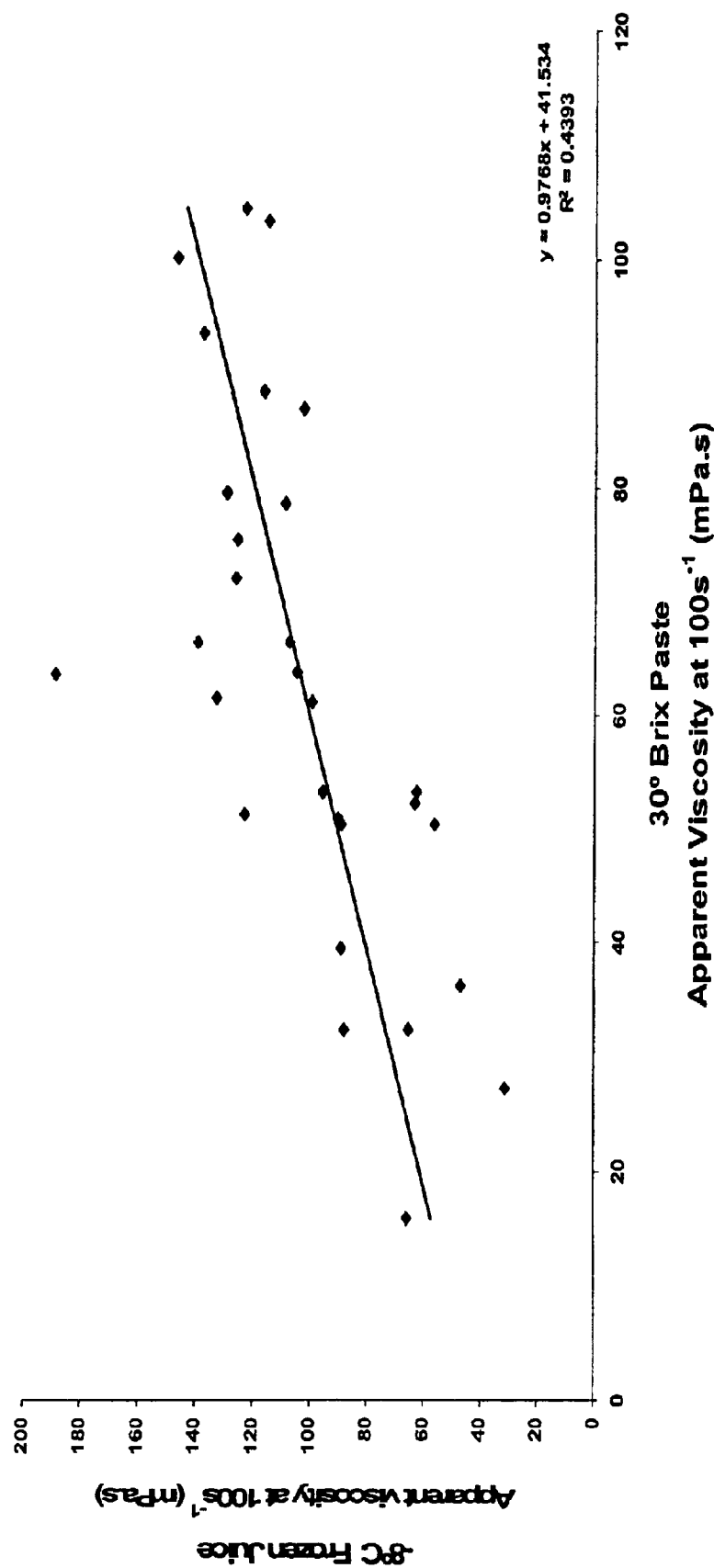
FIG. 13 illustrates data showing apparent viscosity at shear rate 100 s$^{-1}$ of 30° Brix concentrates diluted to original ° Brix versus apparent viscosity of −8° C. pseudo-concentrated juices.
Figure 16:
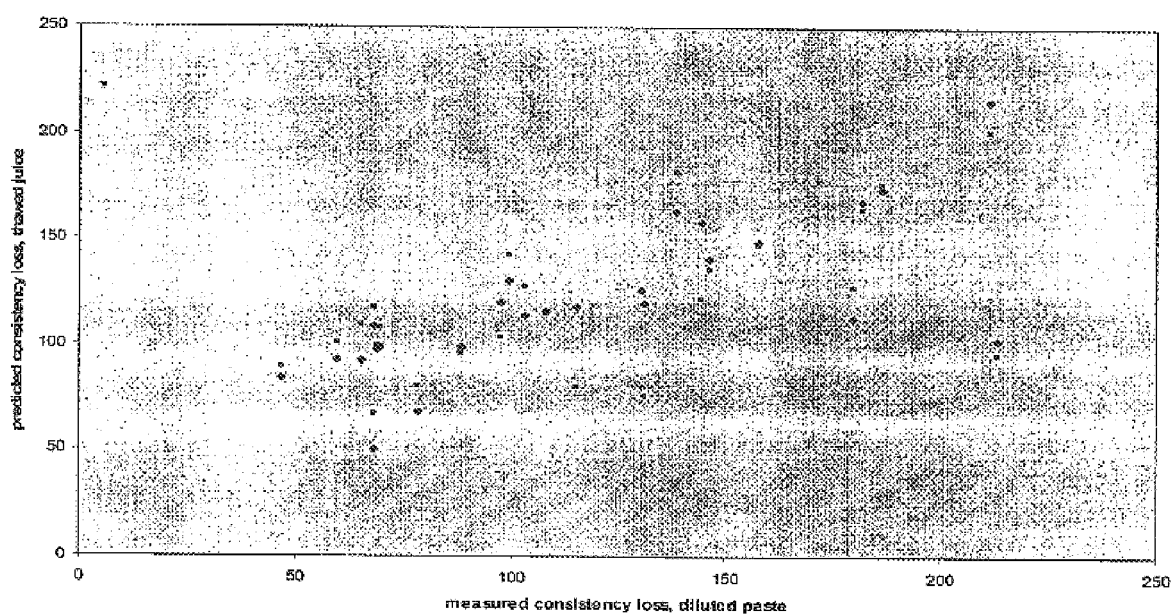
FIG. 16 illustrates data showing the estimated consistency loss (original juice—estimated diluted paste) compared to the measured consistency loss (original juice—measured diluted paste) at −5° C. and 50 s$^{-1}$.
Figure 17:
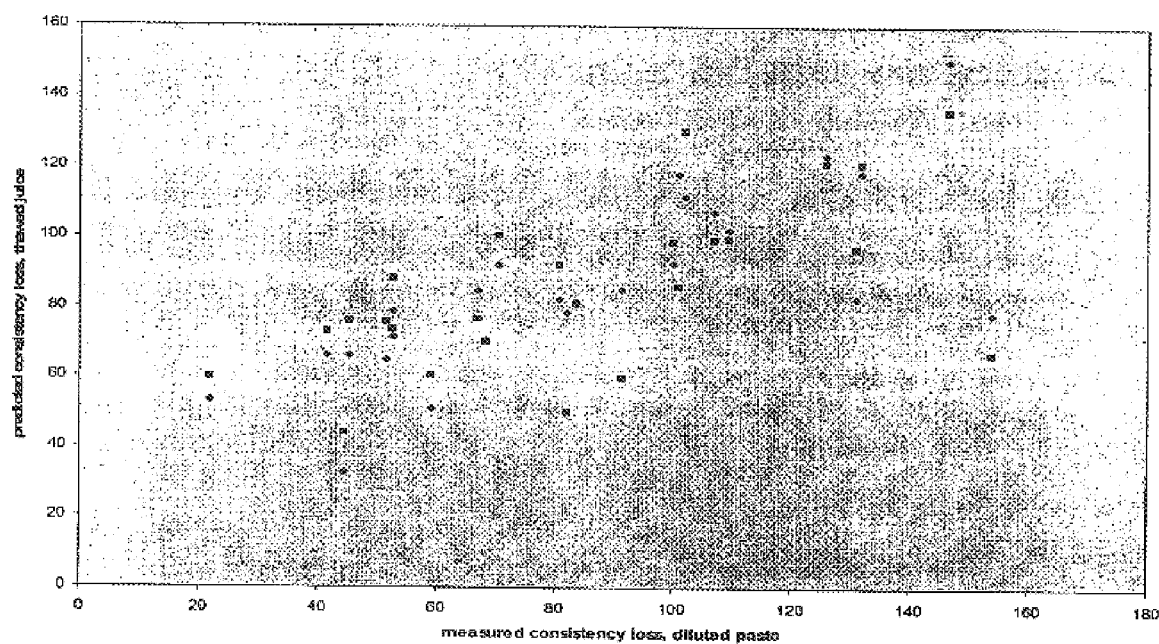
FIG. 17 illustrates data showing the estimated consistency loss (original juice—estimated diluted paste) compared to the measured consistency loss (original juice—measured diluted paste) at −8° C. and 50 s$^{-1}$.
Figure 18:
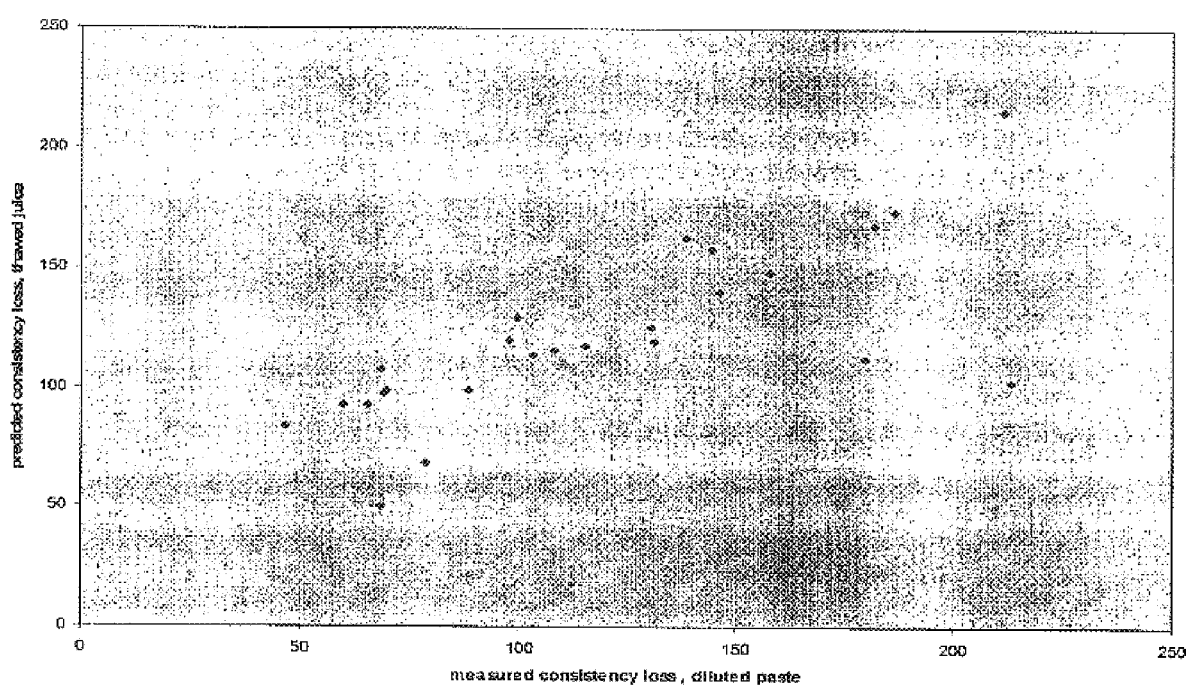
FIG. 18 illustrates data showing the estimated consistency loss (original juice—estimated diluted paste) compared to the measured consistency loss (original juice—measured diluted paste) at −5° C. and 100 s$^{-1}$.
Figure 19:
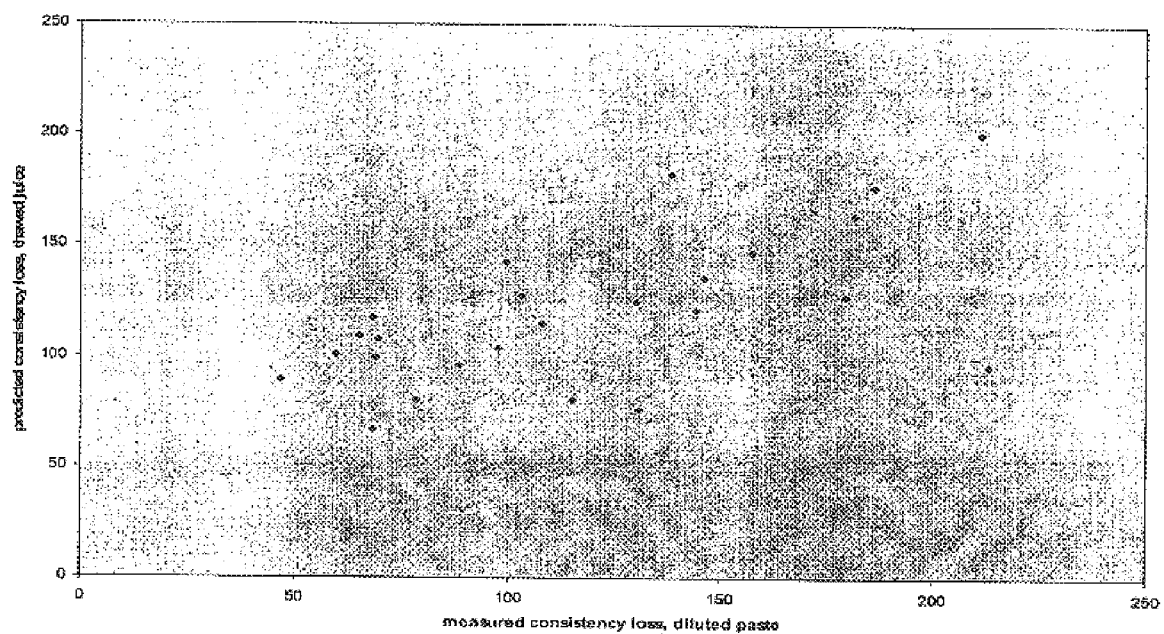
FIG. 19 illustrates data showing the estimated consistency loss (original juice—estimated diluted paste) compared to the measured consistency loss (original juice—measured diluted paste) at −8° C. and 100 s$^{-1}$.
Figure 20:
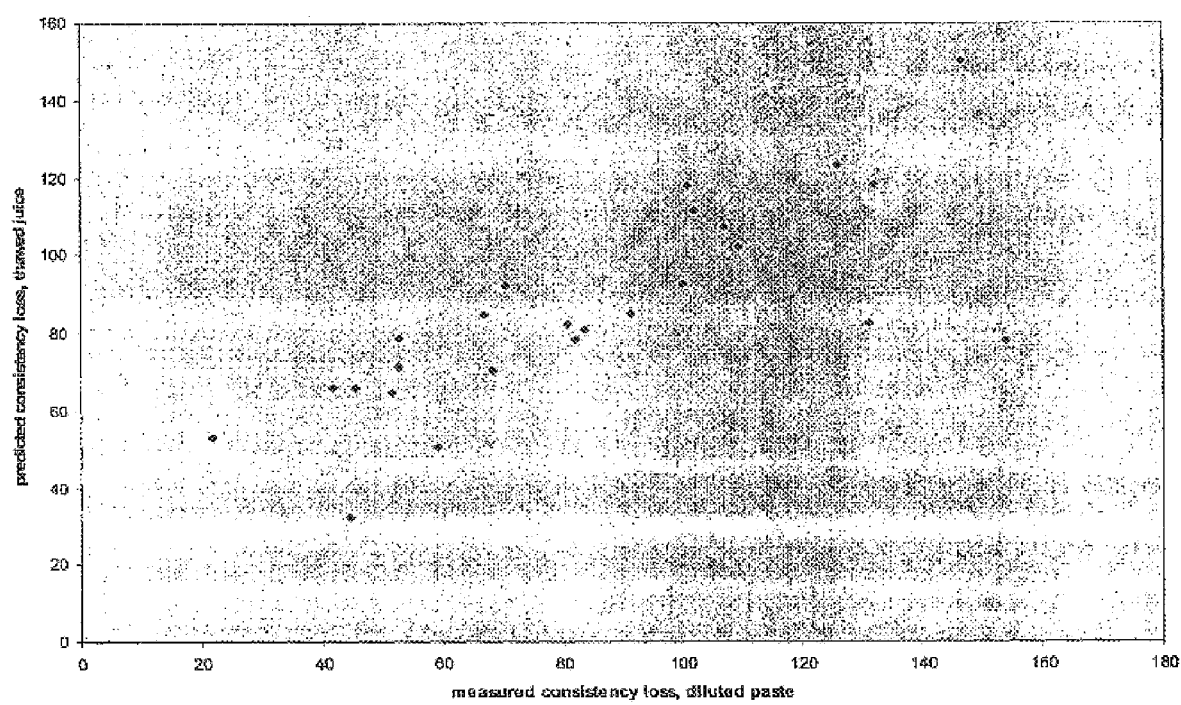
FIG. 20 illustrates data showing the estimated consistency loss (original juice—estimated diluted paste) compared to the measured consistency loss (original juice—measured diluted paste) at −5° C., −8° C., and 50 s$^{-1}$.
Figure 21:
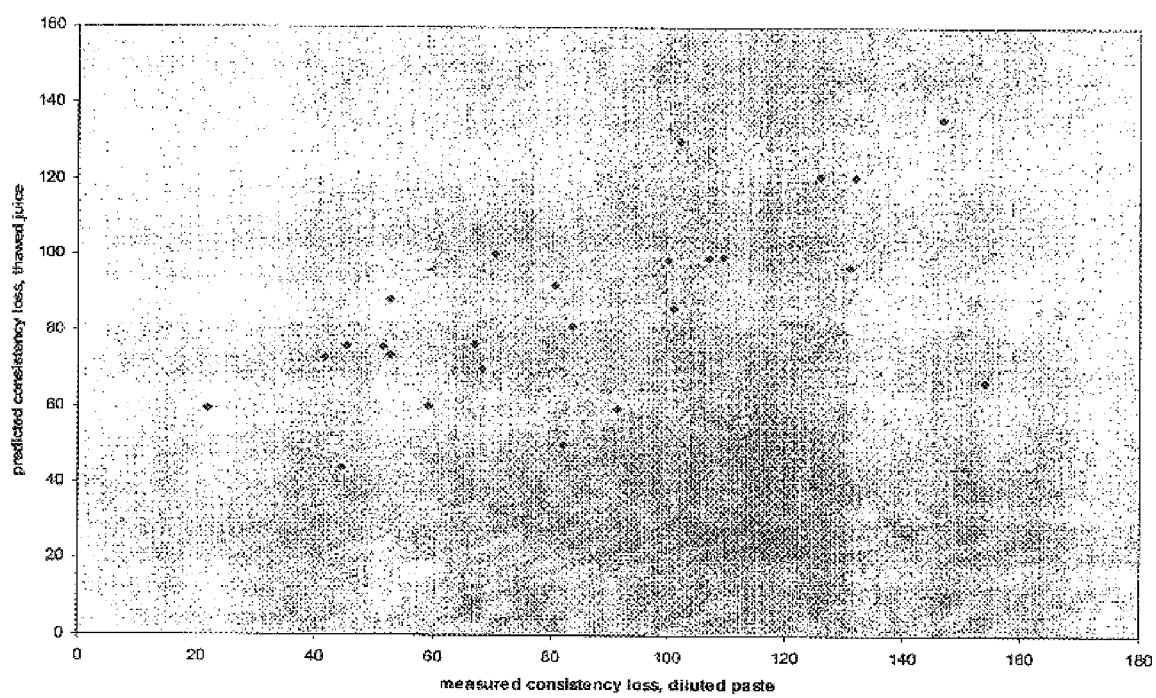
FIG. 21 illustrates data showing the estimated consistency loss (original juice—estimated diluted paste) compared to the measured consistency loss (original juice—measured diluted paste) at −5° C., −8° C., and 100 s$^{-1}$.
Figure 2:
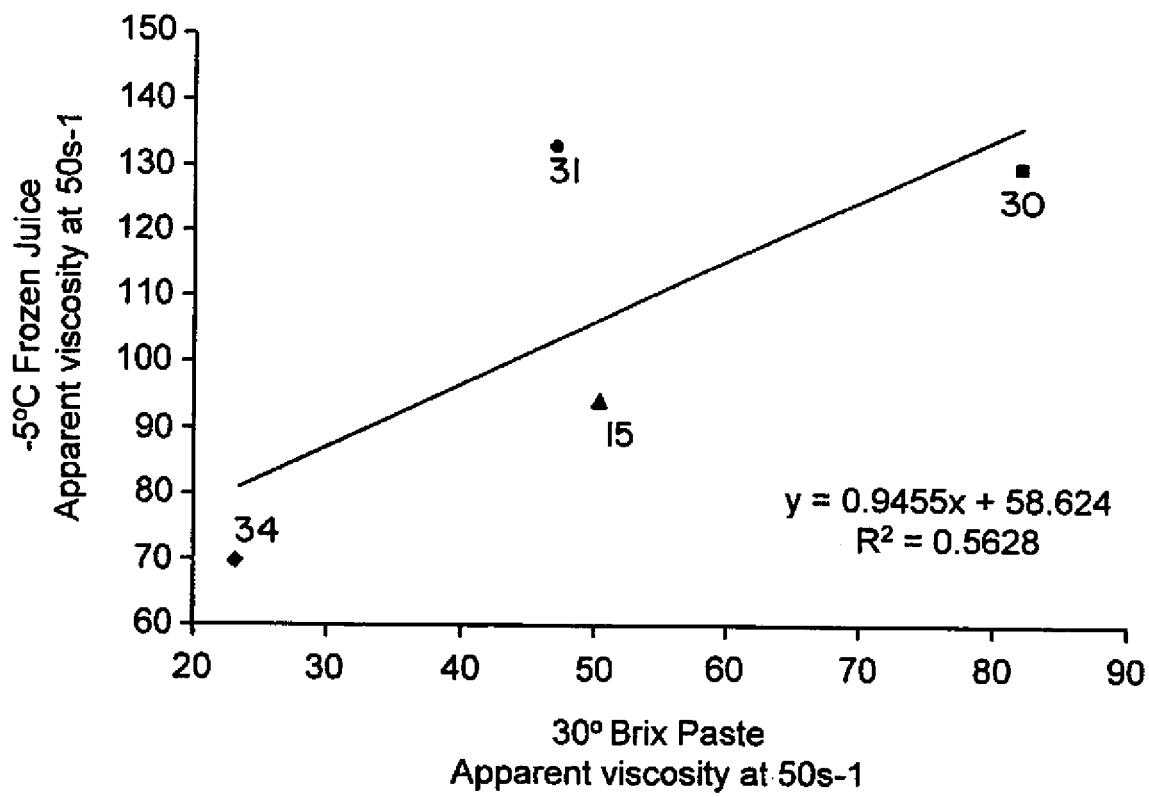
Figure 3:
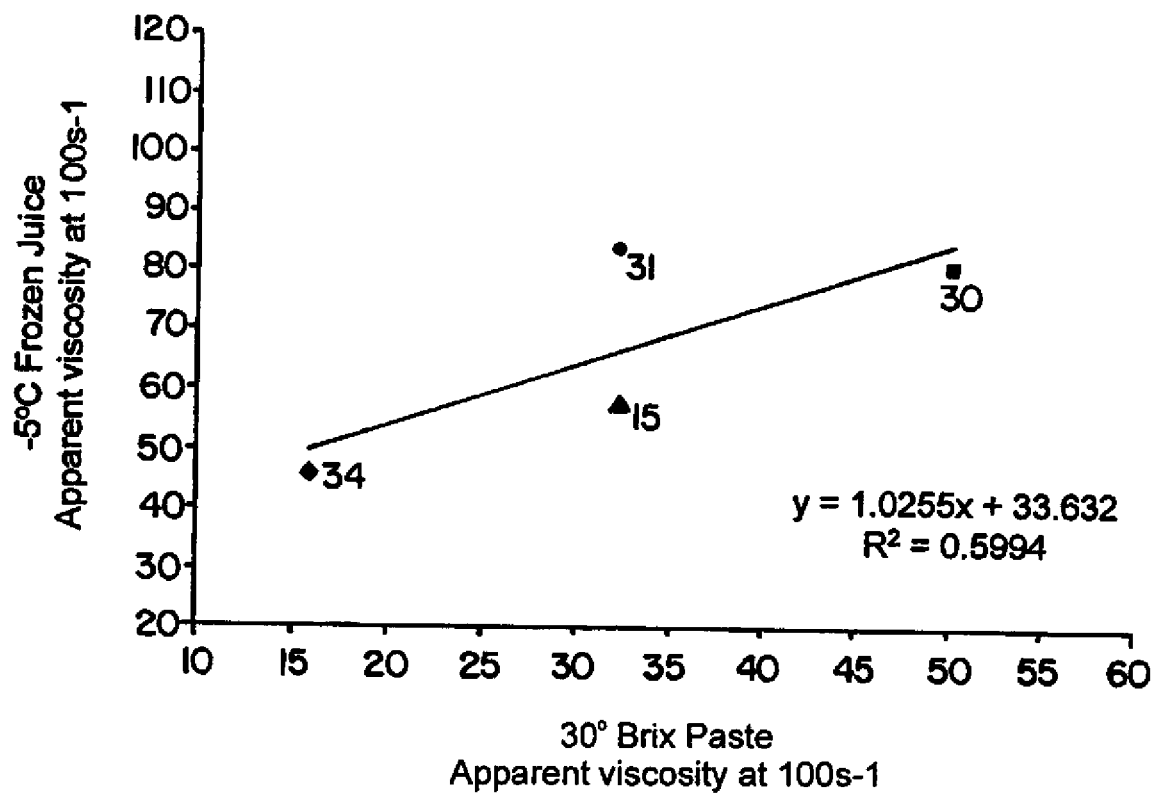
Figure 4:
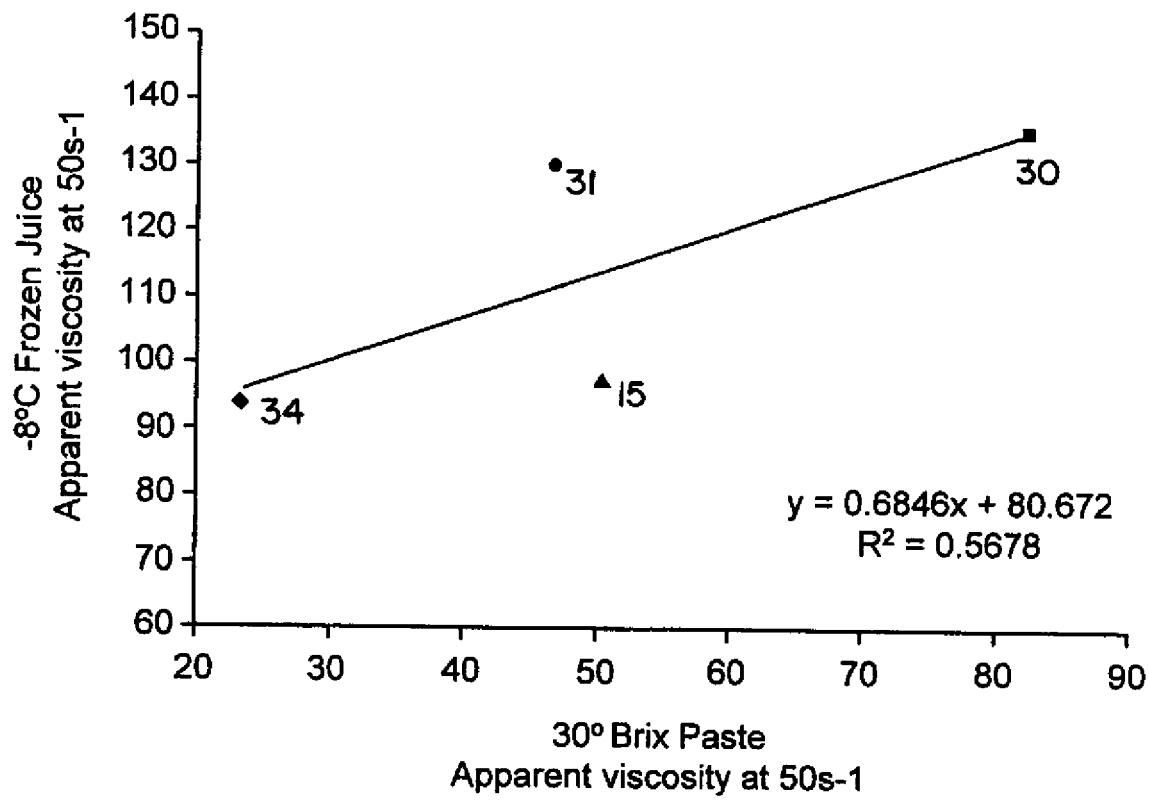
Figure 5:
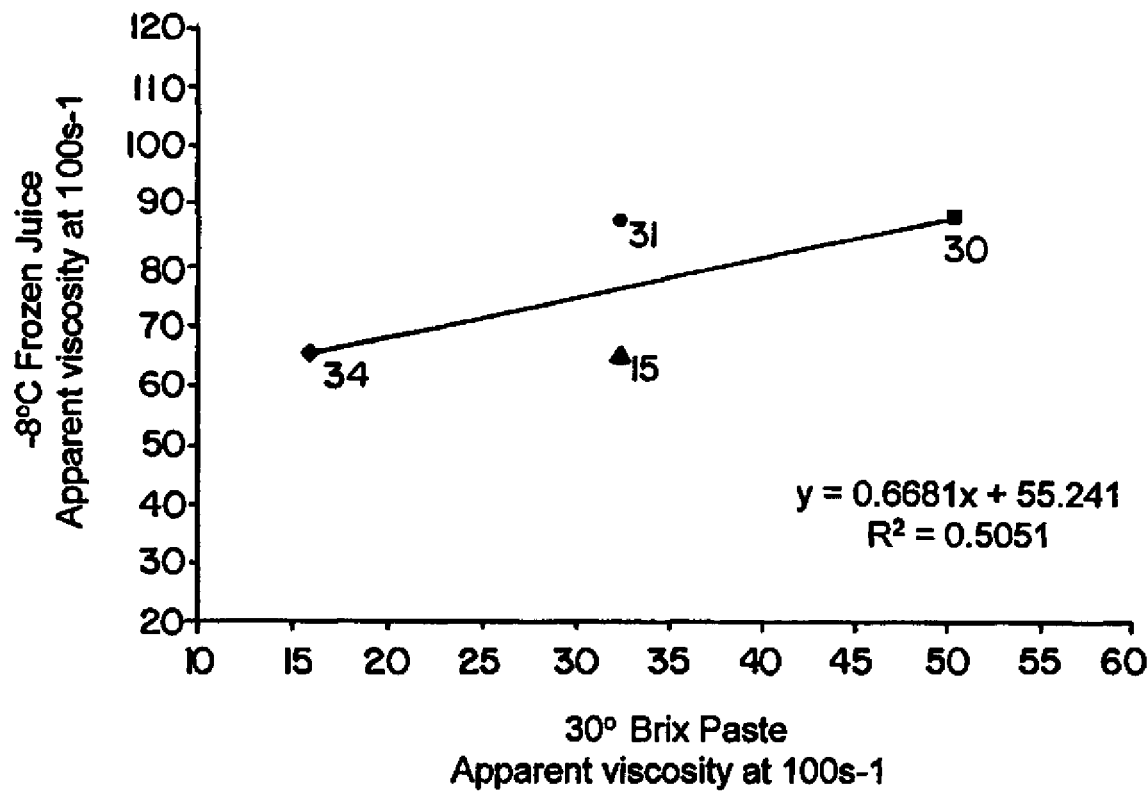

The present invention provides a rapid and efficient method for predicting the amount of yield loss when a fruit or vegetable puree is concentrated and reduced to a fruit or vegetable paste. The methods of the present invention are useful for screening new varieties of fruits and vegetables to predict their potential yield loss. The methods of the present invention are also useful for predicting yield loss when additives are included in a fruit or vegetable puree. The methods of the present invention are particularly useful for predicting the yield loss associated with the concentration and reduction of tomato puree into tomato paste.

II. Definitions

"Fruit" as used herein refers to usually edible reproductive body of a plant. Exemplary fruits include berries, stone fruits, compound fruits, and pome fruits.

"Vegetable" as used herein refers to any part of a plant that is not a fruit. Exemplary vegetables include leaves, roots, stalks, stems, or a combination thereof.

"Puree" as used herein refers to a fluid mixture of solids and liquid prepared from fruit or vegetables, wherein the fluid mixture has substantially the same percentage of solids as the original, unprocessed fruit or vegetable. Alternately, a puree may refer to a concentrate of a fluid mixture of solids and liquid prepared from fruit or vegetables, wherein the fluid mixture has a higher or lower percentage of solids as the original, unprocessed fruit or vegetable. A puree may be made from fresh, dried, or frozen fruits or vegetables. A puree may be made from a single type of fruit or vegetable or multiple types of fruits or vegetables. A puree may contain additional additives such as salts, sugars, acids, bases, preservatives, flavoring agents.

"Paste" as used herein refers to a puree prepared from fruit or vegetables, wherein the puree has a higher percentage of solids as the original, unprocessed fruit or vegetable, as a result of removing water, e.g., by evaporation or any other means known in the art. A paste typically contains about 25%, 35%, 45%, 55%, 65%, 75%, or 85% fruit or vegetable solids. A paste may be made from fresh, dried, or frozen fruits or vegetables. A paste may be made from a single type of fruit or vegetable or multiple types of fruits or vegetables. A paste may contain additional additives such as salts, sugars, acids, bases, preservatives, flavoring agents.

"Viscosity" or "consistency" as used herein refers to the resistance to change in form exhibited by liquids and by liquids mixed with solids. "Viscosity" or "consistency" refer to the flow characteristics of the liquid or liquids mixed with solids. "Viscosity" or "consistency" also refer to the degree of separation of free liquid from the solids.

"Freezing" as used herein refers to subjecting a puree to temperatures sufficient to induce conversion of the puree from a liquid phase to a frozen solid phase. Typically the temperature is chosen to correspond to the desired ° Brix for the form in which the puree will be transported. "° Brix" as used herein refers to the hydrometer scale for sugar solutions so graduated that its readings at a specified temperature represent percentages by weight of sugar in the solution.

"Thawing" as used herein refers to subjecting the frozen puree to temperatures sufficient to induce conversion of the frozen puree to a liquid phase.

"Measuring" as used herein refers to determining the viscosity of a fruit or vegetable puree. The measurement may be determined using a consistometer or a viscometer.

"Comparing viscosity" as used herein refers to determining the difference between the viscosity of a puree that has never been frozen and thawed with the viscosity of a puree that has been frozen and thawed. The percentage difference between the viscosity of the puree provides a measurement of the level of solids required for the reconstituted product to have substantially the same consistency as the puree.

"Power law equation" as used herein refers to an equation used to calculate the shear stress or force required to change the form of a non-Newtonian liquid or fluid. The following equation represents a typical power law calculation: $\sigma = K\gamma^n + \sigma_o$. $\sigma$ represents the shear stress or force required to change the form of the liquid. K represents a viscosity coefficient. $\gamma$ represents the shear rate or amount of force applied to the liquid. n represents the power law exponent, a constant that relates to the shear characteristic of the liquid. For shear thickening liquids (i.e., fluids that increase their resistance to changes in form as force is exerted on them), n>1. For shear thinning liquids (i.e., fluids that decrease their resistance to changes in form as force is exerted on them), n<1. For Newtonian liquids, n=1.

"Rheology" is the study of the response of materials to applied forces. While ideal solids deform elastically and the original shape is recovered upon removal of the applied stress, ideal fluids deform irreversibly under stress—they flow. Elastic materials have a "memory" for the original shape. During elastic deformation of an "ideal solid", the energy required for the deformation is stored and completely recovered once the applied stress is removed. The energy required to deform an "ideal fluid", on the other hand, is dissipated as heat and cannot be recovered. The rheological behavior of any real material falls between the two extremes of the ideal solid and the ideal fluid. A material with such a combination of viscous and elastic behaviour is termed "viscoelastic."

This work is primarily concerned with fluids, which are characterized by the free movement of volume elements among themselves. The response of a fluid to an applied force is commonly described by its viscosity, which is defined as the ratio of resistance of the fluid to shear to the rate of shear. A continuous input of energy is necessary to maintain flow, i.e., the flow between an upper plate and a bottom plate. The bottom plate is stationary. A represents the interface of the liquid layer next to the upper plate, which is moving. A force F is applied to the area A and causes it to move at the velocity $v_{max}$. The shear stress $\sigma$ is defined as:

$$\sigma = \frac{F}{A} \quad (1)$$

The applied shear stress causes the flow pattern. There is a velocity gradient across the gap between the two plates. The velocity is zero at the stationary plate and is highest at the upper boundary. The rate of deformation (shear rate) is simply the velocity gradient across the liquid layers.

The dependence of the shear rate on the stress necessary to maintain flow is $$\dot{\gamma} = \frac{dv}{dh} \quad (2)$$

described by flow curves. These flow behavior models can be modeled by the following power-law expression:

$$\sigma - \sigma_0 = k\dot{\gamma}^n \quad (3)$$

In the limiting case of a Newtonian fluid, the zero-shear stress, $\sigma_0$, is zero and the flow behavior index, n, is unity. The value k is a measure for the fluid's viscosity and is termed "consistency coefficient". Newtonian fluids are characterized by a proportional relationship between shear stress, $\sigma$, and shear rate, $\dot{\gamma}$. Thus, the consistency coefficient, k, of Newtonian fluids becomes the shear-rate independent absolute viscosity coefficient $\eta$. In the case of shear-thinning (pseudo-plastic) fluids, the flow curve is non-linear and a single viscosity coefficient cannot be assigned. The viscosity $\eta$ is shear rate-dependent and is termed "apparent viscosity". There are two ways to define the apparent viscosity. As used herein, "apparent viscosity" is the ratio of shear stress and shear rate. Another definition is the derivative of the shear stress with respect to the shear rate.

$$\eta(\dot{\gamma}) = nk\dot{\gamma}^{n-1} \quad (5)$$

$$\eta = \frac{\sigma}{\dot{\gamma}} \quad (4)$$

where $\eta(\dot{\gamma})$ is the apparent viscosity given by the slope of the flow curve. For shear thinning fluids, the apparent viscosity decreases with increasing shear rate. In a logarithmic coordinate system, the relationship between the apparent viscosity and the shear rate follows a straight line over wide ranges of shear rates. The line has a slope of n−1 and intersects the ordinate at nk. In the case of shear-thinning fluids, the value of the flow behavior index is in the range of 0<n<1. The flow behavior index decreases with increasing shear-thinning character of the fluid. For example, tomato juice is a shear-thinning dispersion of solid matter in a fluid medium. Thus, the parameter n can be used to characterize the degree of shear thinning. Most foods are shear-thinning or Newtonian, as opposed shear thickening (n>1).

The Bingham plastic and Herschel-Bulkley flow behavior models show a solid-like behavior until the applied stress reaches a threshold value, at which the material starts to flow. This threshold is termed "yield stress", $\sigma_0$. Any force applied to the material that does not exceed the yield stress value does not cause flow but elastic deformation.

"Yield loss" or "consistency loss" as used herein refers to the loss of solid material associated with concentration reduction of fruit or vegetable purees into fruit or vegetable pastes prior to their utilization in the manufacture of a desired product. "Case yield" as used herein refers to the amount of final product produced from a given amount of initial raw material. Yield loss indicates that fewer units of final product are produced from the same amount of initial raw material.

"Concentration" or "reduction" as used herein refers to the removal of liquids from fruit or vegetable purees to make fruit or vegetable paste.

"Reconstitution" or "dilution" as used herein refers to the addition of liquid to a fruit or vegetable paste. Any amount of liquid may be added provided it is sufficient to produce the desired consistency or viscosity. The amount of liquid added may be the same or may be more or less than the amount of liquid required to bring the volume of the reconstituted or diluted paste to the volume of the fruit or vegetable puree from which the paste was made.

III. Predicting Yield Loss in a Fruit or Vegetable Puree

A. Preparing the Puree

A fruit or vegetable puree can be made by any means known in the art. Typically, a tomato puree is prepared by the method known in the art. For example, the puree can be prepared using the hot break or cold break method. In the hot break method, tomatoes are macerated and heated immediately after maceration to inactivate any enzymes. In the cold break method, tomatoes are macerated, held at room temperature to allow enzymes to act, and then heated. Either the hot break or cold break methods may be used to prepare a puree on an industrial scale or on a smaller scale.

A puree may be prepared from, for example, fresh fruit or vegetables, peeled or whole fruit or vegetables, chopped, diced, sliced, or macerated fruit or vegetables, previously frozen fruit or vegetables, or dried and reconstituted fruit or vegetables. A puree may be made from a single type of fruit or vegetable or multiple types of fruits or vegetables. For example, a tomato puree may be made from a single variety of tomato or from multiple varieties of tomatoes. A tomato, onion and garlic puree may also be prepared. A puree may contain additional additives such as salts, sugars, acids, bases, preservatives, flavoring agents, protease inhibitors, pectins, and gels. The pH of the puree may be buffered using, for example, citric acid/sodium citrate, gluconic acid/sodium gluconate, acetic acid/sodium acetate, or malic acid/sodium malate systems. For example, a tomato based puree may contain edible acids such as, citric acid, malic acid, lactic acid, acetic acid, or gluconic acid. Suitable flavoring agents include, for example, table salt, sucrose, onion, garlic, black pepper, red pepper, basil, oregano, thyme, bell pepper, celery, bay leaf, fennel, and parsley. Methods of preparing tomato purees are described in U.S. Pat. Nos. 6,004,591 and 5,869,122.

B. Freezing the Puree

Typically the fruit or vegetable puree is frozen at about −4° C. to about −20° C. Preferably the fruit or vegetable puree is frozen at about −6° C. to about −12° C. Even more preferably the fruit or vegetable puree is frozen at about −8° C. Those of skill in the art will understand that the fruit or vegetable puree may be frozen at any temperature that substantially corresponds to a particular ° Brix desired for the fruit or vegetable paste. As defined above, ° Brix refers to the hydrometer scale for sugar solutions so graduated that its readings at a specified temperature represent percentages by weight of sugar in the solution. Thus, the ° Brix measurement relates to the concentration of sugar in the fruit or vegetable paste. The correspondence between the frozen storage temperature and ° Brix can be determined for each fruit and vegetable puree using by methods known in the art. For example, using methods known in the art, it has been determined that freezing a tomato puree at −8° C. provides a viscosity measurement that is predictive of yield loss for a tomato paste of 28–30 ° Brix and freezing a tomato puree at −4° C. provides a viscosity measurement that is predictive of yield loss for a tomato paste of 10–15° Brix.

A skilled artisan will also understand that the puree may be frozen using any means known in the art. For example, the puree may be frozen using a standard freezer unit as is known in the art.

C. Comparing the Puree Viscosity

The viscosity of the fruit or vegetable puree may be measured by any means known in the art. Typically, a consistometer or viscometer is used to measure the viscosity of a puree. Any consistometer or viscometer that collects data at multiple shear rates may be used provided that its capacity is suitable for the sample size. Suitable consistometers and viscometers include, for example, Ostwald Viscometers, Cannon-Fenske Viscometers, Lamb Capillary Viscometers, Continuous Puree Consistometers, rotational MacMichael Viscometers, Brookfield Viscometers, Vibratory Viscometers, Zahn Viscometer, Haake Rotovisko Viscometers, Hoeppler Viscometers, Adams Consistometers, and Rotovisco Rheometers. For examples, a sample of thawed puree is place inside the chamber of the consistometer or viscometer that operates at multiple shear rates. A detector on one portion of the chamber measures the rate of flow as pressure is exerted on the sample. Based on the rate of flow of the puree through the chamber, the consistometer or viscometer provides measurements corresponding to the K (viscosity) and n (power law exponent) values for the power law equation. The power law equation can then be used to describe the relationship between shear rate and shear stress.

Typically the viscosity of the original fruit or vegetable puree is measured, frozen as described above, and the viscosity of the thawed fruit or vegetable puree is measured. The thawed fruit or vegetable puree may have a lower or higher same consistency or viscosity than the original fruit or vegetable puree. Alternately, the thawed fruit or vegetable puree has substantially the same consistency or viscosity than the original fruit or vegetable puree. The percentage difference in the consistency or viscosity of the original puree and the consistency or viscosity of the thawed puree provides a measurement for the amount of starting material required to make the fruit or vegetable paste. The relationship between consistency loss and yield loss is linear and can be summarized as follows: (consistency loss)=(coefficient)×(yield loss). For example, if the thawed puree has 5% lower consistency or viscosity compared to the original puree, (5% more starting material)×(coefficient) will be needed to produce a paste that reconstitutes or dilutes to the same consistency as the original puree. Any method known in the art can be used to determine the coefficient. For example, the consistency of tomato paste samples is measured at multiple solids levels, e.g., 5%, 6%, and 7%. The consistency is plotted against the level of solids to identify the coefficient.

EXAMPLES

The following examples are offered to illustrate, but not to limit the claimed invention.

Example 1

Materials and Methods

An appropriate quantity of tomatoes is washed, trimmed, and chopped (i.e., macerated). Tomato puree is then prepared by heating 900–1000 grams of macerated tomatoes. Water is added to the heated, macerated tomatoes to bring the total volume back to the volume of the unheated macerated tomatoes. The mixture is homogenized, degassed, and put into plastic bags. The samples are then heated in boiling water for 9 minutes and sealed. For Bench Scale screening of the tomato purees, a tomato paste is made from the tomato puree using methods known in the art. The tomato paste is then rediluted to the original volume of the tomato puree. The viscosity of the original tomato puree and the rediluted tomato paste are taken to determine the yield loss. For Freeze screening of the tomato purees, the tomato puree is frozen for at least 48 hours before viscosity measurements are taken. The viscosity of the original tomato puree and the frozen thawed tomato puree are taken to determine the yield loss. Viscosity measurements are taken using a Rotovisco Rheometer.

Example 2

Comparison of Freeze Screening and Bench Scale Screening

Tomato puree was prepared from three samples of different tomato types as described above. For analysis of Freeze screening, the tomato puree was then frozen at −8° C. for 48 hours. For Bench Scale screening, the tomato puree was concentrated into a tomato paste, then rediluted to the original volume of the puree.

Table 1 illustrates results from the comparison of bench scale screening method versus the freeze screening method with three separate tomato samples. These results demonstrate that both the Bench Scale screen and the Freeze screen are predictive of the yield loss.

| Sample | Viscosity (fresh) | Viscosity (Bench Scale screen) | Viscosity (Freeze screen) |
|--------|-------------------|--------------------------------|---------------------------|
| A | 1.543 | 1.108 | 0.918 |
| B | 1.473 | 1.008 | 0.840 |
| C | 0.990 | 0.806 | 0.602 |

Example 3

Effect of Frozen Temperatures on the Loss of Viscosity in Tomato Juice

This example describes experiments to evaluate the effect of pseudo-concentration at −5, −8, −12 and −22° C. on the loss of viscosity in tomato juice and compares the results to the effect of conventional concentration to obtain 30° Brix paste followed by subsequent re-dilution.

Materials and Methods

Tomato juice: tomato juice from cultivars 15, 30, 31 and 34 were obtained from Seminis Vegetable Seeds, Inc. in Woodland, Calif.

Paste manufacture: Degassed tomato juice was concentrated using a scraped-surface type bench scale concentrator by direct evaporation. The concentrator consists of a glass cylinder fitted with a stirring device with four plastic blades. The stirring device was used to keep the juice agitated and the blades to scrape concentrated paste from the surface of the cylinder. The whole device was immersed in a water bath with the temperature maintained at 50° C. to provide energy for evaporation. A vacuum of 740 mm Hg was applied to the system resulting in lowering the boiling point of juice to about 20° C. Samples were retrieved at approximately 12, 20, 25 and 30 ° Brix concentration levels. Concentrates were treated with sodium azide at a concentration of 0.02% to retard spoilage and stored at 4° C. until evaluation. For apparent viscosity measurements, the concentrates were reconstituted with deionized water to the original degree Brix. Care was taking, to produce a homogenous suspension without creating air bubbles. After reconstitution, the samples were allowed to equilibrate for at least 24 hours at 4° C. Then, samples were heated in microwave at no more than 50° C. and equilibrated at 20° C. before evaluation.

Pseudo-concentration: Quadruplicate degassed tomato juice samples were stored in 250 mL plastic containers and pseudo-concentrated at −5, −8, −12 and −22° C. For apparent viscosity measurements, samples thawing were done using a microwave. Care was take to heat the tomato juice at no more than 50° C., samples were equilibrated at 20° C. before evaluation.

Degree Brix: Refractive index measurements were used to determine the degree Brix on degassed tomato juice (control) and on reconstituted tomato juice from tomato concentrates at 20° C. using a RFM 80 digital refractometer (Bellingham & Stanley Ltd., Kent, England).

Apparent viscosity: A Rotovisco RV20 rheometer (Haake Buchler Instruments, Inc., Saddle Brook, N.J.) controlled strain rate rheometer fitted with an M5/MVII sensor system was used to measure apparent viscosity at shear rate of 50 s$^{-1}$ ($\eta_{50}$) and 100 s$^{-1}$ ($\eta_{100}$) of tomato juice, reconstituted concentrates to the original degree Brix and thaw pseudo-concentrated juices. The rheometer consists of two coaxial cylinders, with a 2.6 mm gap. The inner cylinder rotates at programmable rates whereas the outer cylinder is stationary. The outer cylinder is jacketed to maintain temperature control via a thermostatic circulator. The rheometer was programmed to shear the sample at 3.5 s$^{-1}$ for 1 min, increase the shear rate linearly from 3.5 s$^{-1}$ to 450 s$^{-1}$ in 3 minutes, shear the sample at 450 s$^{-1}$ for 1 minute, and then decelerate back to 3.5 s$^{-1}$ over an additional 3 minutes. All samples were equilibrated to 20.0±0.1° C.

Apparent viscosity at shear rate 50 s$^{-1}$ and 100 s$^{-1}$ were obtained after dilution to original ° Brix of 15, 30, 31 and 34 pastes. Apparent viscosity was also measured for thawed pseudo-concentrated samples frozen at −5, −8, −12 and −22° C. Average apparent viscosity of quadruplicate measurements for conventional concentration and pseudo-concentration are reported in FIG. 1. The square of the correlation coefficients ($R^2$) between apparent viscosity of diluted 30° Brix pastes and apparent viscosity of thawed −5° C. pseudo-concentrated juices were 0.563 and 0.599 for shear rate 50 s$^{-1}$ and 100 s$^{-1}$, respectively. $R^2$ between apparent viscosity of diluted 30° Brix pastes and apparent viscosity of thawed −8° C. pseudo-concentrated juices were 0.568 and 0.505 for shear rate 50 s$^{-1}$ and 100 s$^{-1}$, respectively. $R^2$ between apparent viscosity of diluted 30° Brix pastes and apparent viscosity of thawed −12° C. and −22° C. psudo-concentrated juices were considerably lower for both shear rates. Differences in apparent viscosity at 50 and 100 s$^{-1}$ of reconstituted 30° Brix pastes in comparison with thawed −5 and −8° C. pseudo-concentrated juices are shown in FIGS. 2 to 5. Compared to the −5 and −8° C. freeze-concentration process, conventional concentration causes a greater consistency loss in reconstituted juices.

Figure 6:
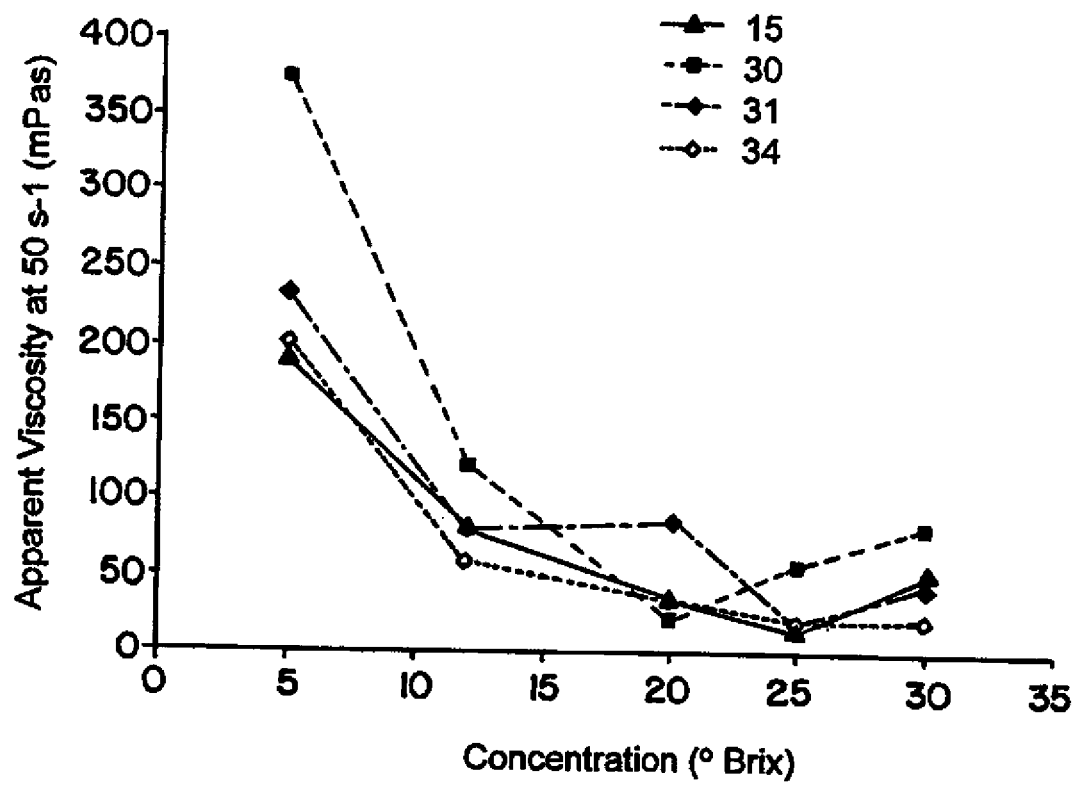
FIG. 6 illustrates data showing changes in apparent viscosity ($\eta_{50}$) of reconstituted tomato juices with the paste concentration.
Figure 7:
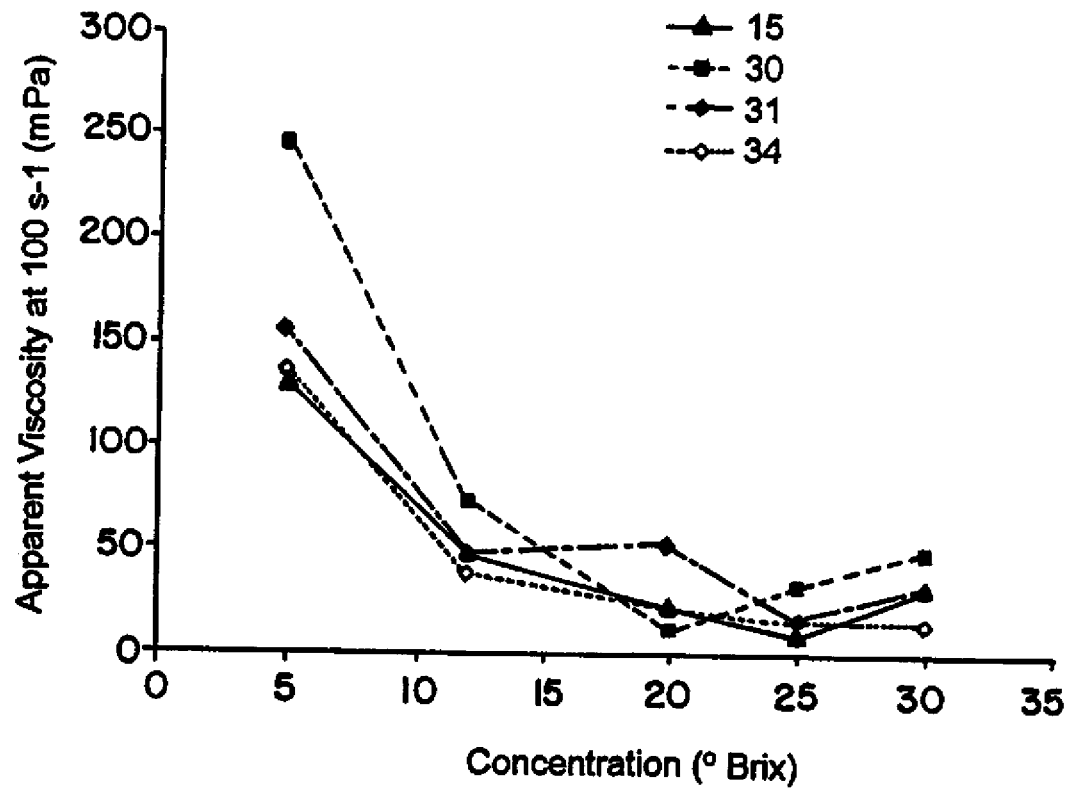
FIG. 7 illustrates data showing changes in apparent viscosity ($\eta_{100}$) of reconstituted tomato juices with the paste concentration.
Figure 10:
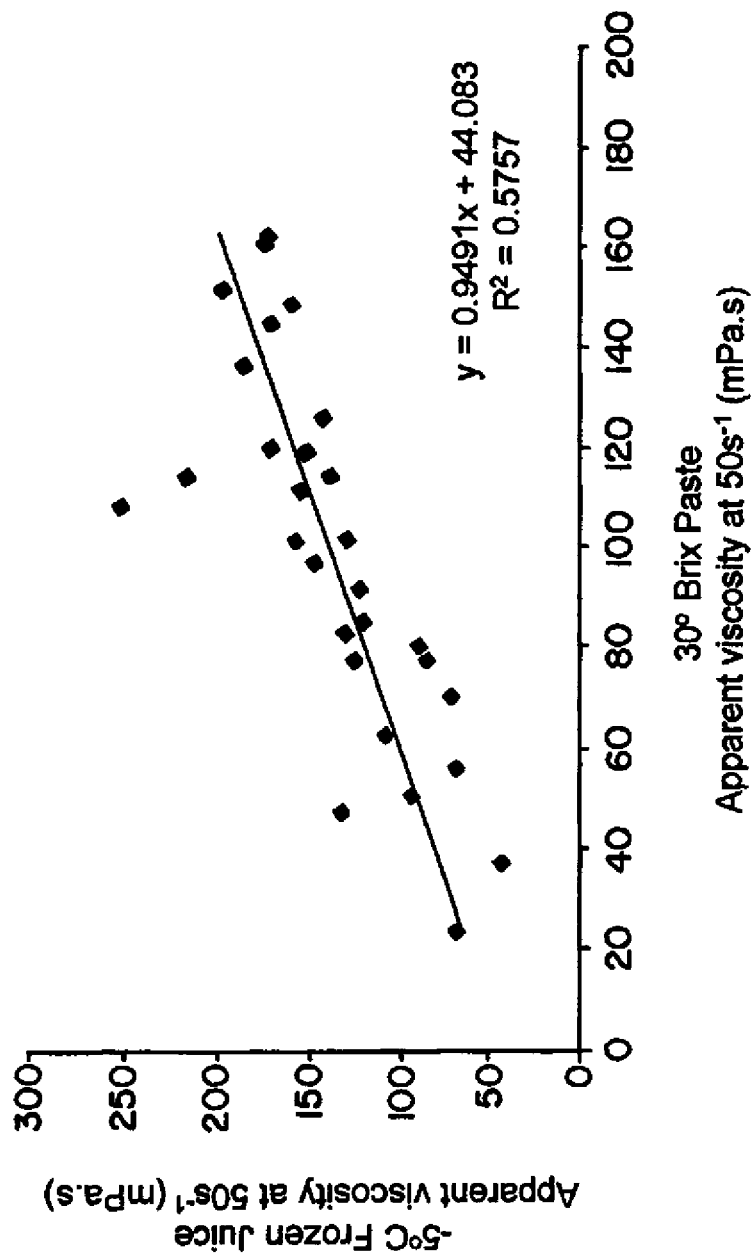
Figure 11:
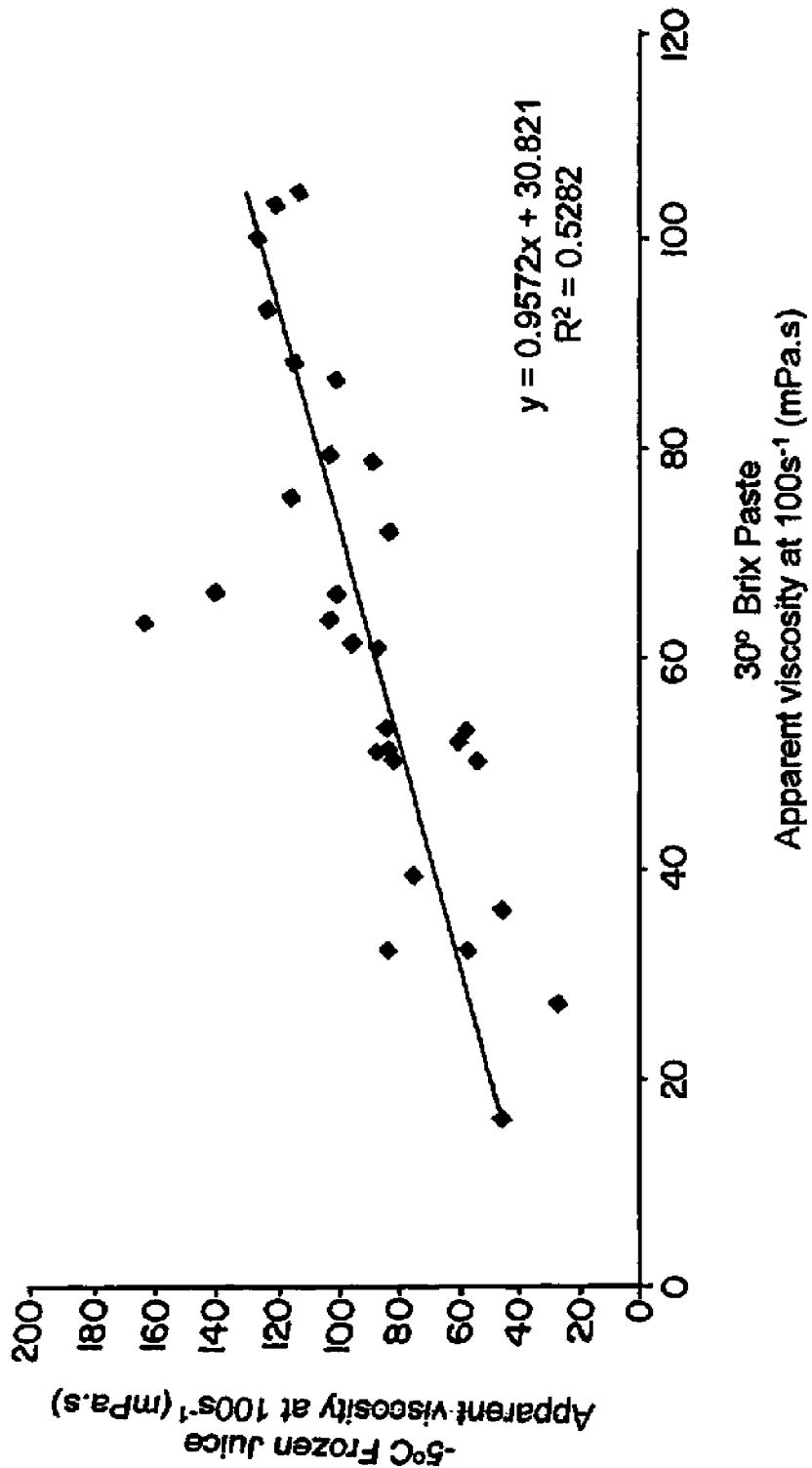
Figure 12:
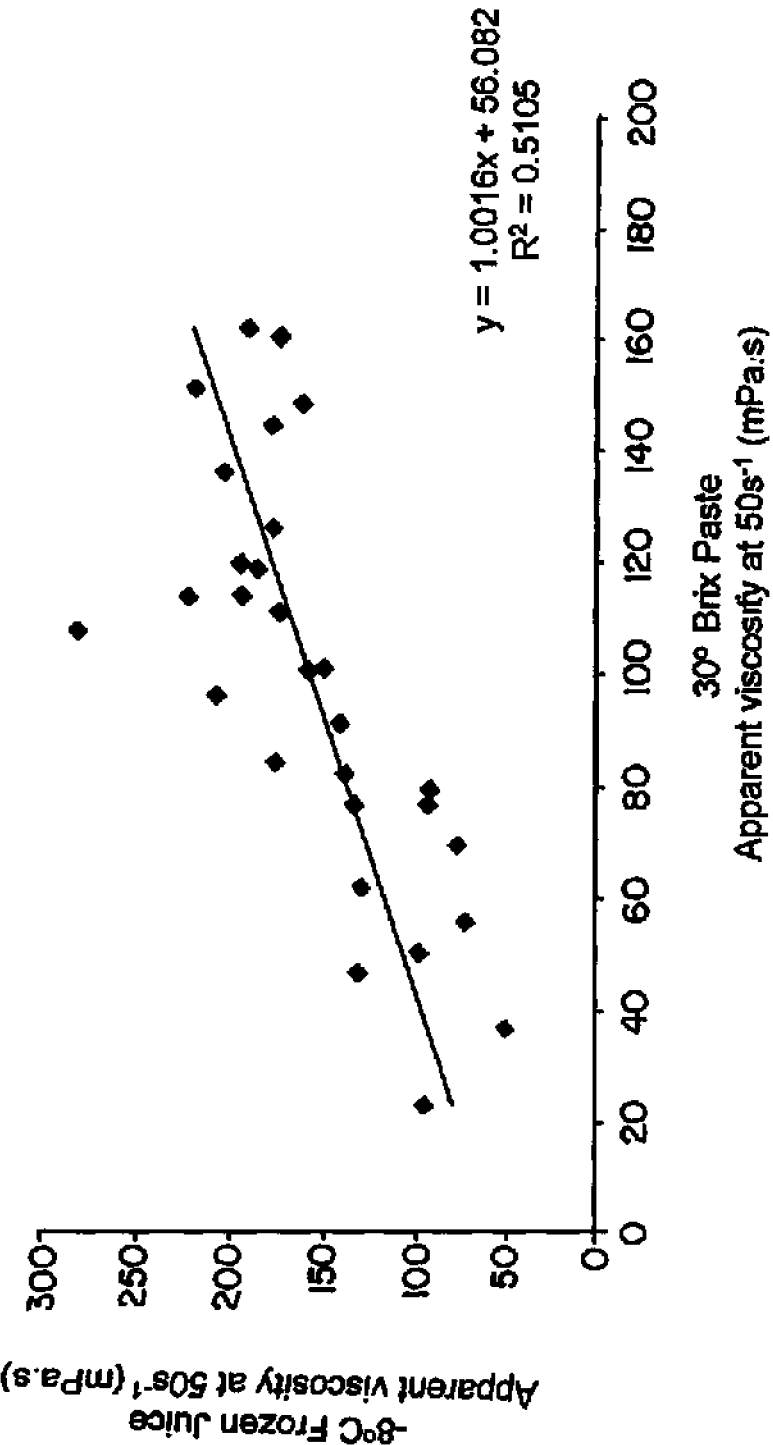
Figure 13:
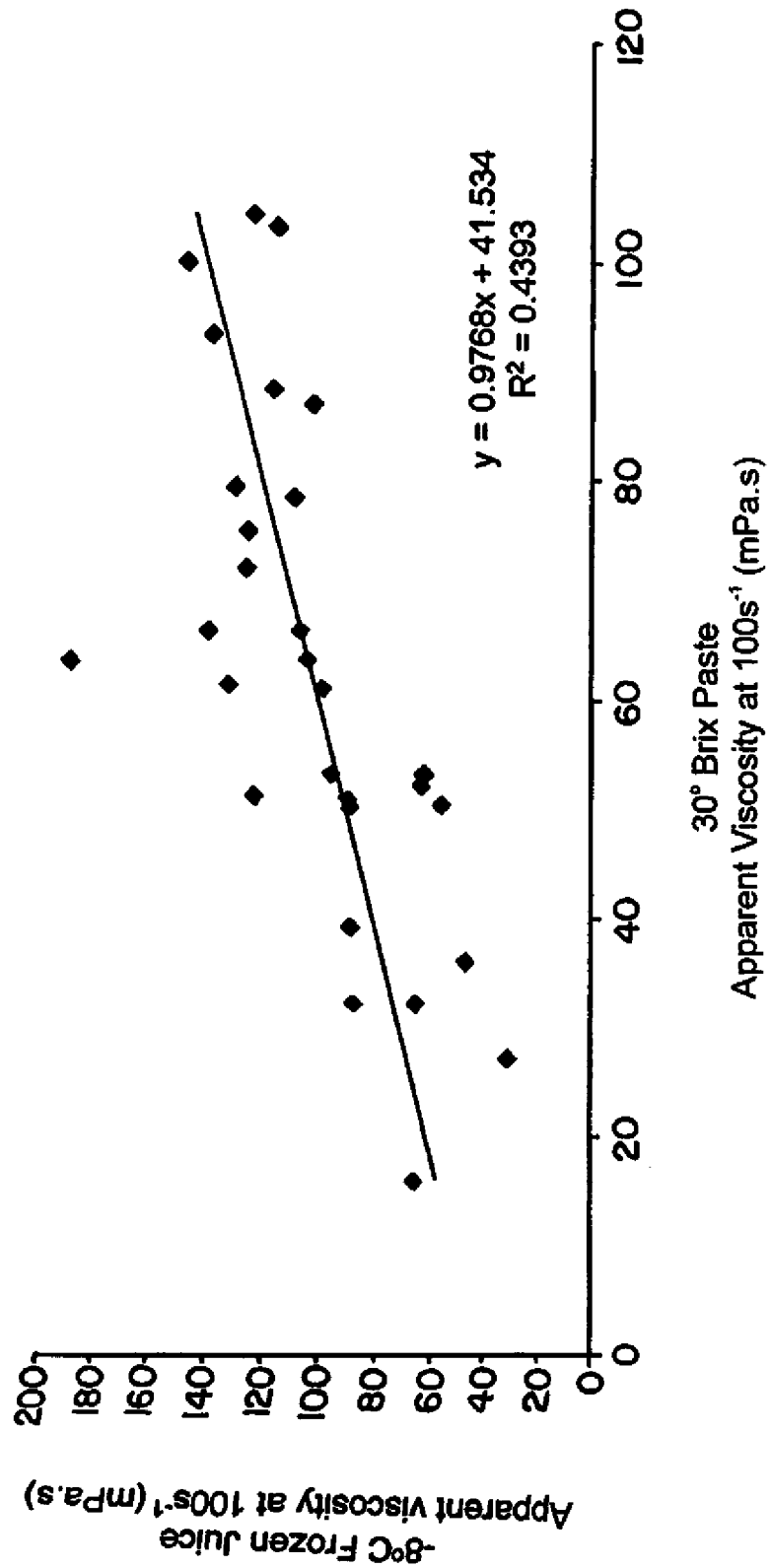
Figure 16:
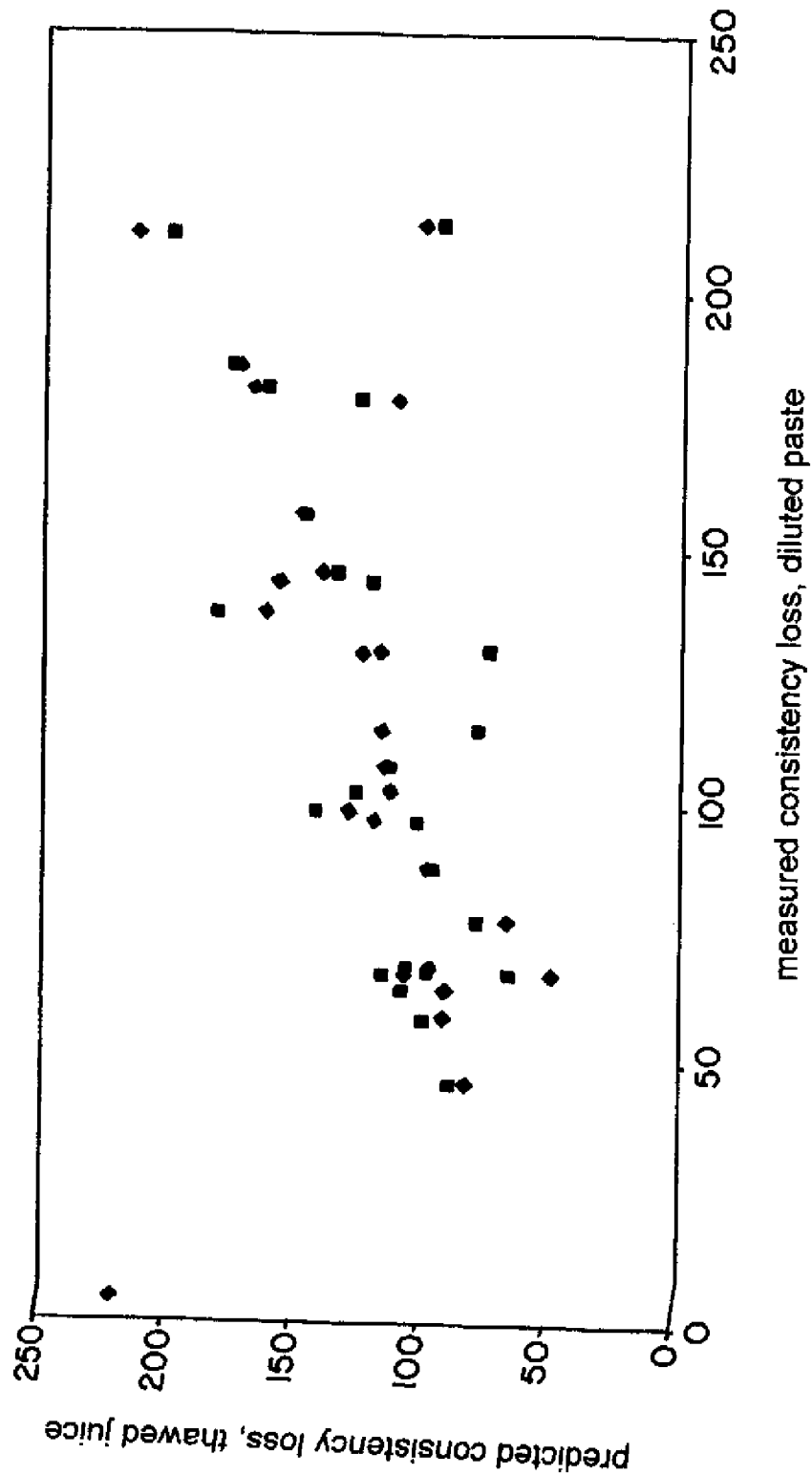
Figure 17:
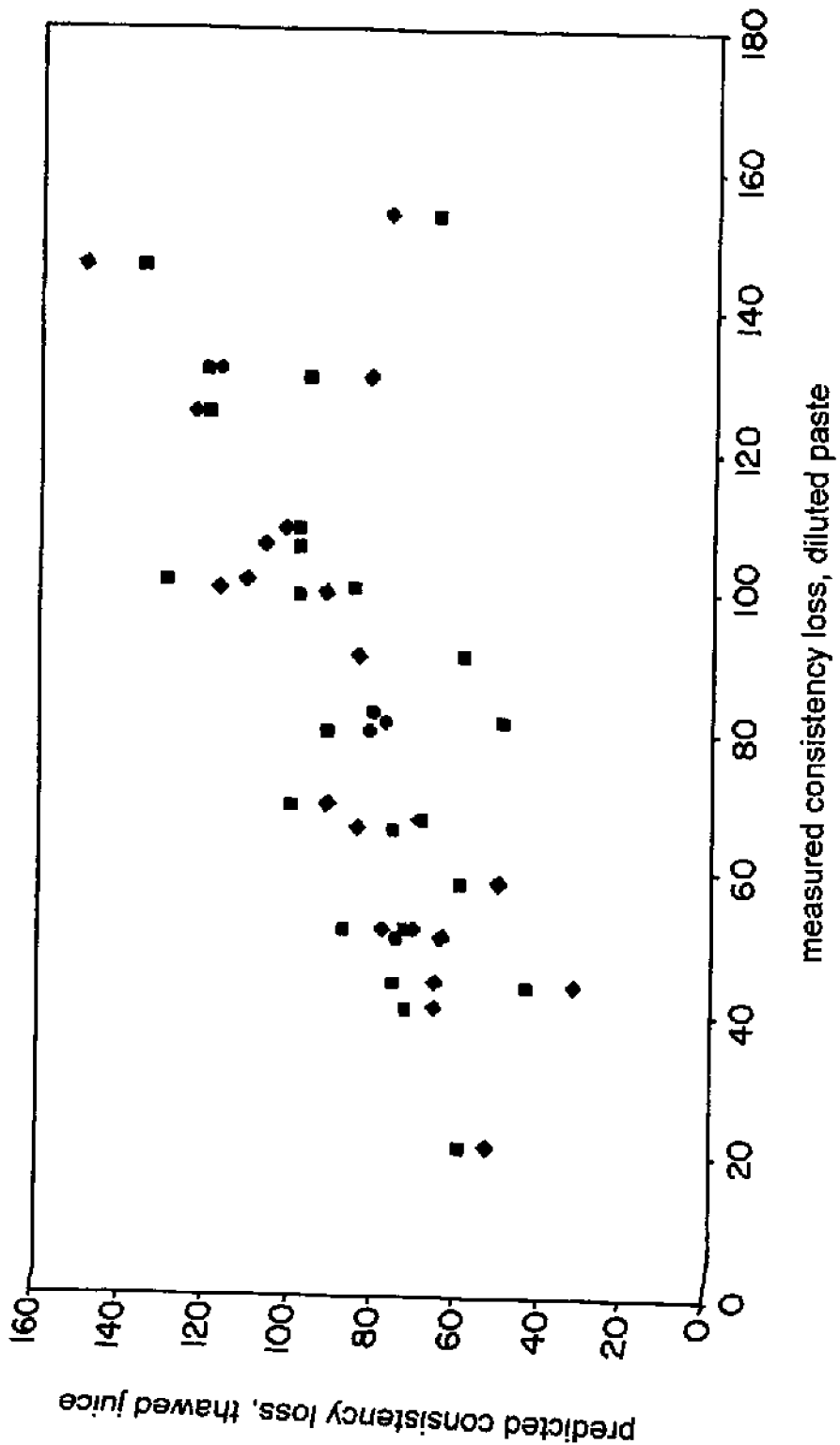
Figure 18:
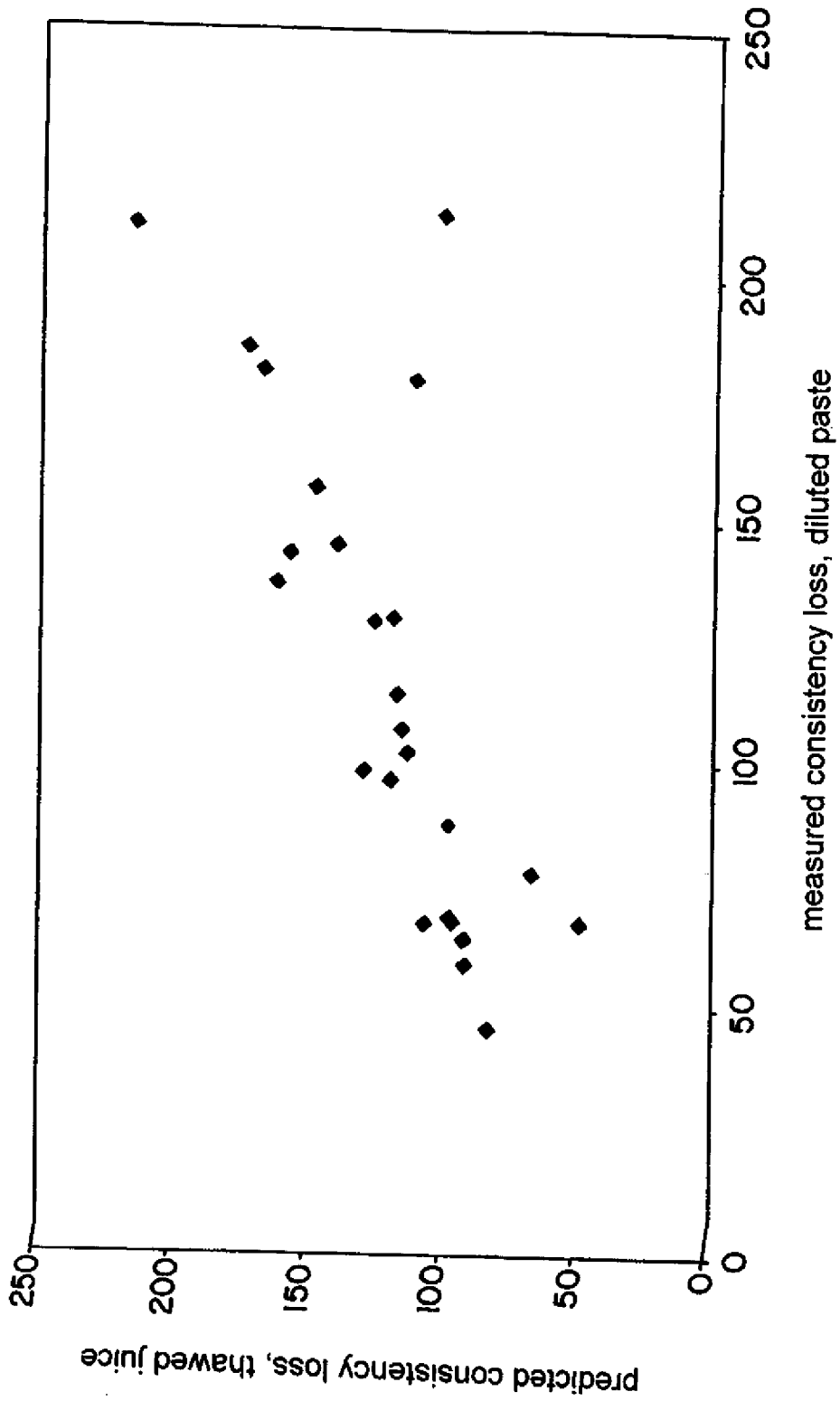
Figure 19:
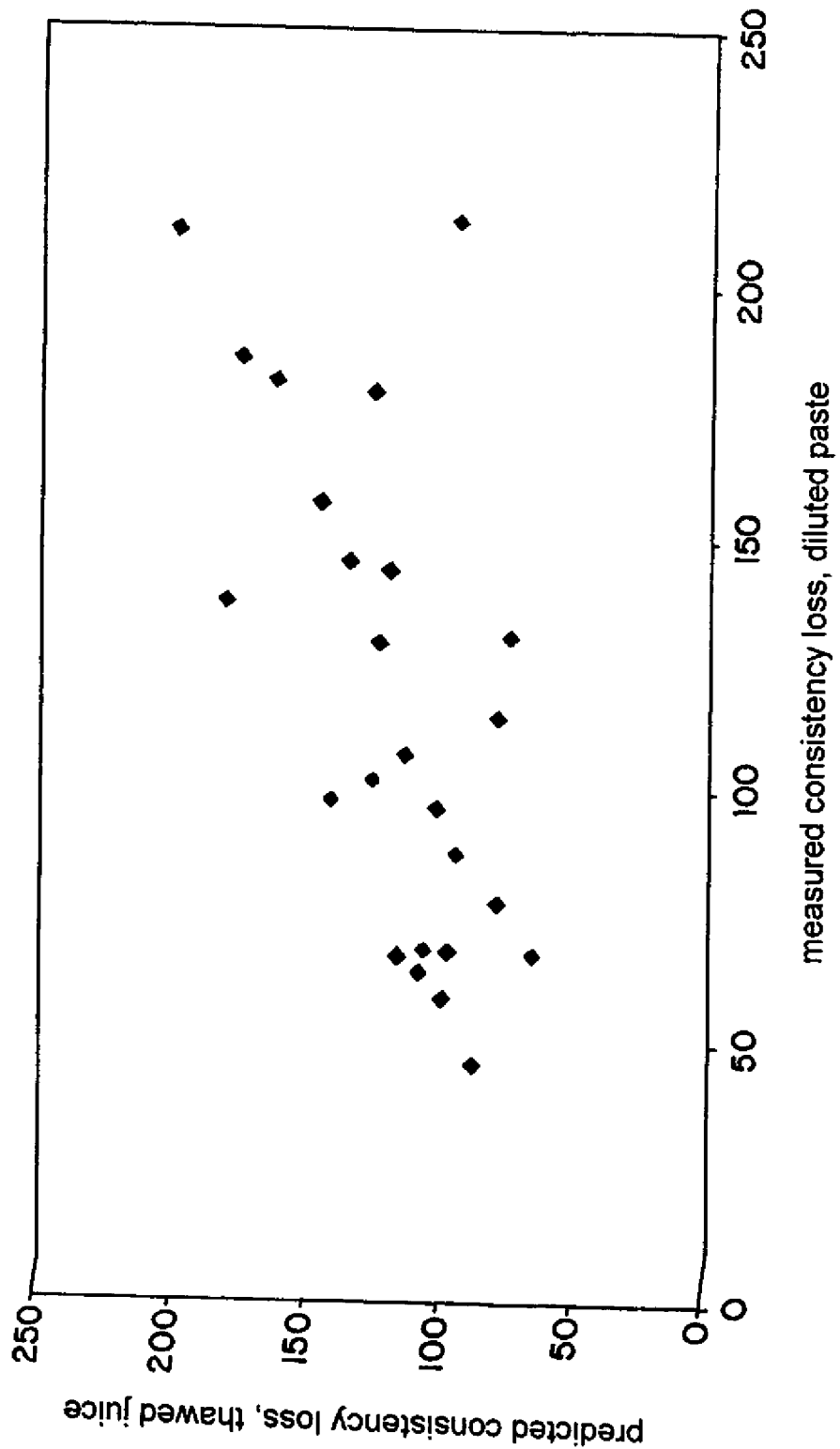
Figure 20:
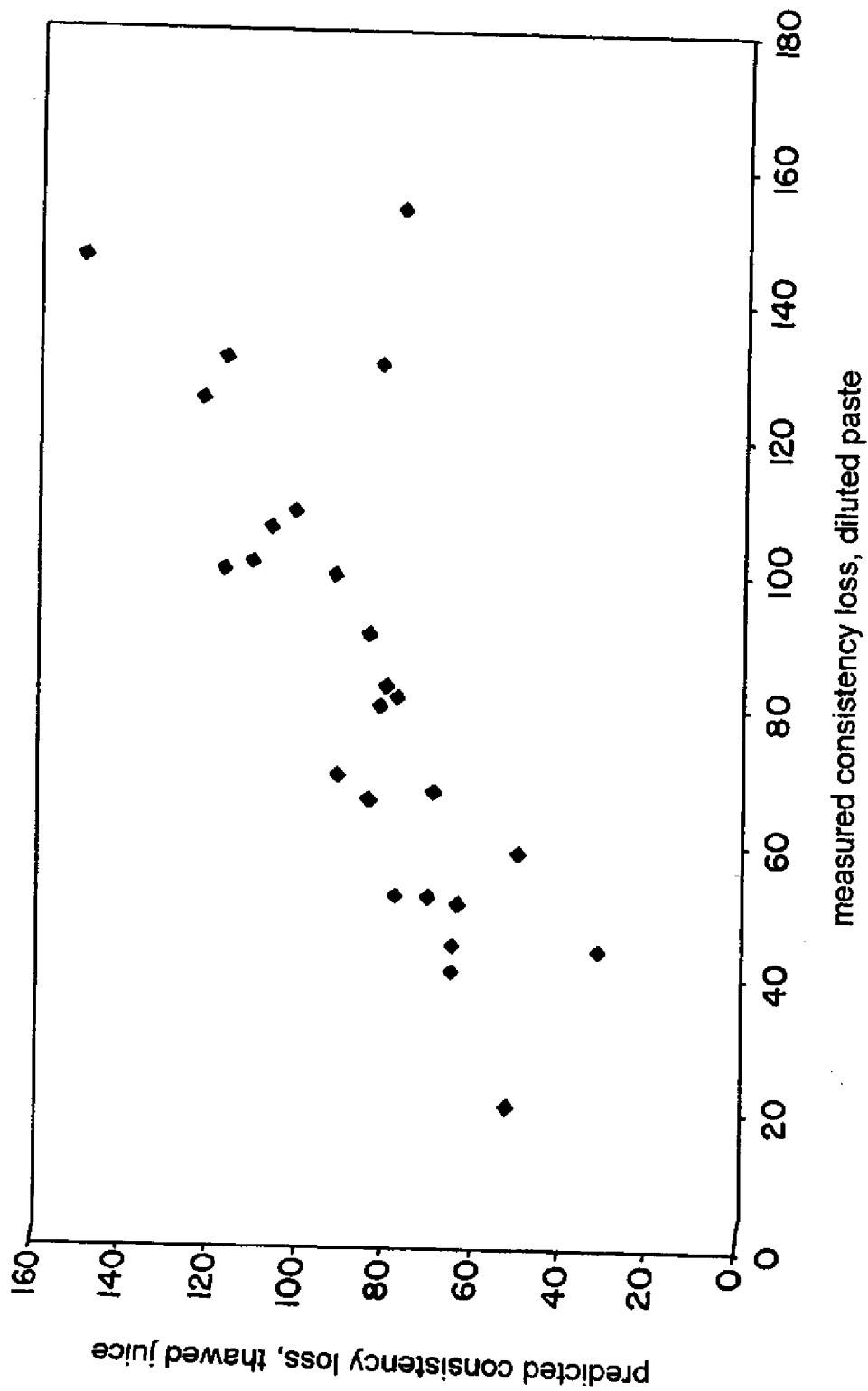
Figure 21:
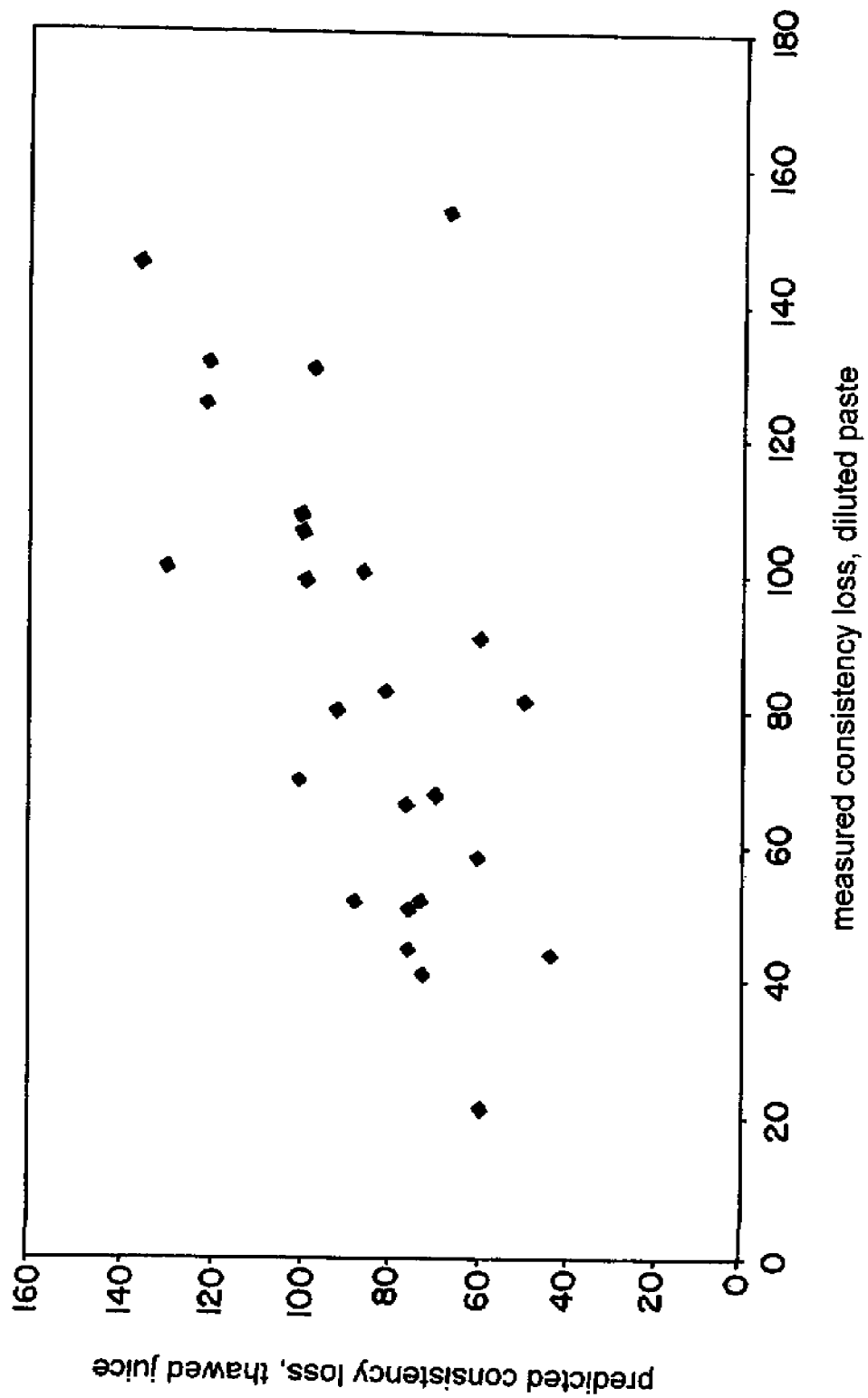

Apparent viscosity at shear rate 50 s$^{-1}$ and 100 s$^{-1}$ were obtained after dilution to original ° Brix of pastes produced from cultivars 15, 30, 31 and 34 concentrated at 12, 20, 25 and 30° Brix. The consistency loss is found to increase with the increase in ° Brix of the paste. In FIGS. 6 and 7, the apparent viscosities at 50 and 100 s$^{-1}$ of juices from cultivars 15, 30, 31 and 34 reconstituted from pastes of varying degrees of concentration are compared to the viscosity of the control juices, which had never been concentrated.

From FIGS. 2–7, it is concluded that pseudo-concentration at −5° C. or −8° C. is appropriate to enable estimation of the consistency of a diluted paste. Also it is concluded that a 30° Brix paste is the most appropriate for comparison, as at this level of concentration there is considerable viscosity loss upon subsequent dilution, as compared to the original juice.

Example 4

Effect of Storage Time on Apparent Viscosity of Pseudo-Concentrated Tomato Juice This example describes experiments to evaluate the effect of storage time on apparent viscosity of pseudo-concentrated tomato juice.

Materials and Methods

Degassed tomato juice from cultivars 15, 30, 31 and 34 were pseudo-concentrated at −5 and −8° C. Apparent viscosity for each variety was measured after 1 and 6 months and data was compared. Samples were thawed at no more than 50° C. using a microwave; samples were equilibrated at 20° C. before rheological evaluation.

Apparent viscosity: a Rotovisco RV20 rheometer (Haake Buchler Instruments, Inc., Saddle Brook, N.J.) controlled strain rate rheometer fitted with an M5/MVII sensor system was used to measure apparent viscosity at shear rate of 50 s$^{-1}$ ($\eta_{50}$) and 100 s$^{-1}$ ($\eta_{100}$) of thaw pseudo-concentrated juices.

Apparent viscosity at shear rate of 50 s$^{-1}$ and 100 s$^{-1}$ for thawed pseudo-concentrated juice from cultivars 15, 30, 31 and 34 were obtained after 1 month and 6 months of storage at −5° and −8° C. Apparent viscosities at both shear rates were essentially the same for all four varieties at both storage times. There is no effect of storage time on consistency loss. Data are shown in FIG. 9.

Example 5

Comparison of the Prediction of Pseudo-Concentration at −5° C. and −8° C. with the Results of Small Scale Conventional Concentration to a Concentration of 30° Brix This example describes experiments to compare the prediction of pseudo-concentration at −5° C. and −8° C. with the results of small scale conventional concentration to a concentration of 30° Brix.

Materials and Methods

Tomato juice: Tomato juices from cultivars 15, 30, 31, 34 and 25 cultivars of 5500 series were obtained from Seminis Vegetable Seeds, Inc. in Woodland, Calif. Degassed tomato juices were concentrated at 30° Brix using a scraped-surface type bench scale concentrator by direct evaporation and by pseudo-concentration at −5 and −8° C.

Paste manufacture: Degassed tomato juices were concentrated at 30° Brix using a scraped-surface type bench scale concentrator by direct evaporation. Concentrates were treated with sodium azide at a concentration of 0.02% to retard spoilage and stored at 4° C. until evaluation. For apparent viscosity measurements, the concentrates were reconstituted with deionized water to its original degree Brix. Care was taking to produce a homogenous suspension without creating air bubbles. After reconstitution, the samples were allowed to equilibrate for at least 24 hours at 4° C. Then, samples were heated in microwave at no more than 50° C. and equilibrated at 20° C. before evaluation.

Pseudo-concentration: Quadruplicate degassed tomato juice samples were stored in 250 mL plastic containers and frozen at −5, −8° C. For apparent viscosity measurements, samples thawing were done using a microwave. Care was take to heat the tomato juice at no more than 50° C., samples were equilibrated at 20° C. before evaluation.

Degree Brix: Refractive index measurements were used to determine the degree Brix on degassed tomato juice (control) and on reconstituted tomato juice from tomato concentrates at 20° C. using a RFM 80 digital refractometer (Bellingham & Stanley Ltd., Kent, England).

Apparent viscosity: A Rotovisco RV20 rheometer (Haake Buchler Instruments, Inc., Saddle Brook, N.J.) controlled strain rate rheometer fitted with an M5/MVII sensor system was used to measure apparent viscosity at shear rate of 50 s$^{-1}$ ($\eta_{50}$) and 100 s$^{-1}$ ($\eta_{100}$) of tomato juice, reconstituted concentrates to its original degree Brix and thaw pseudo-concentrated juices. The rheometer was programmed to shear the sample at 3.5 s$^{-1}$ for 1 min, increase the shear rate linearly from 3.5 s$^{-1}$ to 450 s$^{-1}$ in 3 minutes, shear the sample at 450 s$^{-1}$ for 1 minute, and then decelerate back to 3.5 s$^{-1}$ over an additional 3 minutes. All samples were equilibrated to 20.0±0.1° C.

Apparent viscosity at shear rate 50 s$^{-1}$ and 100 s$^{-1}$ were obtained after dilution to original ° Brix of 15, 30, 31, 34 and 5500 series pastes. Apparent viscosity was also measured for thawed pseudo-concentrated samples frozen at −5, −8° C. Average apparent viscosity of quadruplicate measurements for conventional concentration and of 12 measurements for pseudo-concentration is shown in FIGS. 14A and 14B.

Compared to the −5 and −8° C. freeze-concentration process, conventional concentration causes a greater consistency loss in reconstituted juices.

The square of the correlation coefficients ($R^2$) between apparent viscosity of reconstituted 30° Brix pastes and apparent viscosity of thawed −5° C. pseudo-concentrated juices were 0.5757 and 0.5282 for shear rate 50 s$^{-1}$ and 100 s$^{-1}$, respectively. $R^2$ between apparent viscosity of reconstituted 30° Brix pastes and apparent viscosity of thawed −8° C. pseudo-concentrated juices were 0.5105 and 0.4393 for shear rate 50 s$^{-1}$ and 100 s$^{-1}$, Differences in apparent viscosity at 50 and 100 s$^{-1}$ of reconstituted 30° Brix pastes in comparison with thawed −5 and −8° C. pseudo-concentrated juices are shown in FIGS. 10–13. Cultivars 5563 and 5566 apparent viscosity of −5 and −8 pseudo-concentrated juices fell apart from all other cultivars.

Examples 3–5, in combination, show that there is an acceptable correlation between the consistency of a diluted 30° Brix tomato concentrate, and the consistency of a sample of the original juice following freezing at −5° C. or −8° C., followed by thawing. Hence it is possible, by freezing then thawing a juice sample, to make a reasonable prediction of the consistency to be expected of a reconstituted juice prepared by dilution to the original ° Brix of a paste produced from a juice. Consistency can be expressed in many ways. In these studies, we have reported the apparent viscosity at shear rates of 50 s$^{-1}$ and 100 s$^{-1}$.

In addition to predicting the consistency of a product produced by dilution of a paste prepared from a cultivar, without the need to prepare anything beyond a small amount of a juice sample, it is also helpful to be able to estimate the extent of consistency loss to be expected of a diluted paste as compared to the original juice. It is not appropriate merely to compare the consistency of the original juice and the frozen-thawed juice. The consistency of the frozen-thawed juice is not the same as that of a diluted paste. However, we can use the correlation equation relating the viscosity of the frozen-thawed juice to the viscosity of the diluted paste to estimate, from the consistency of the frozen-thawed juice the consistency to be expected of a diluted paste. The correlation equations for −5° C. and −8° C. at both 50 s$^{-1}$ and 100 s$^{-1}$ are shown in the plots in the reports of the 3 constituent studies. They are also detailed here.

Correlation equations for −5° C.

$$\eta_{50}^f = 0.9491\eta_{50} + 44.08$$

$$\eta_{100}^f = 0.9572\eta_{100} + 30.82$$

Correlation equations for −8° C.

$$\eta_{50}^f = 1.0016\eta_{50} + 56.08$$

$$\eta_{100}^f = 0.9768\eta_{100} + 41.53$$

where $\eta_A^f$ represents the viscosity of frozen-thawed juice at shear rate A s$^{-1}$ and $\eta_A$ represents the viscosity of diluted 30 ° Brix paste at shear rate A s$^{-1}$.

In FIGS. 16–21 are shown plots of the estimated consistency loss (original juice—estimated diluted paste) compared to the measured consistency loss (original juice—measured diluted paste).

The correlation coefficients for these plots are around 0.7. Hence, using the appropriate correlation between frozen-thawed juice consistency and diluted paste consistency, a good estimate of the potential consistency loss to be expected of a variety as a result of processing to paste can be made.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for predicting consistency of a fruit or vegetable paste, said method comprising:

freezing a fruit or vegetable puree at about −4° C. to about −20° C.;

thawing said puree;

measuring viscosity of thawed puree; and comparing the viscosity of said thawed puree with viscosity of original puree, thereby predicting the consistency of the fruit or vegetable paste.

2. The method according to claim 1, wherein the fruit is a tomato.

3. The method according to claim 1, wherein the puree is frozen at about −6° C. to about −12° C.

4. The method according to claim 1, wherein the puree is frozen at about −8° C.

5. The method according to claim 1, wherein the puree is frozen for at least 48 hours before the step of thawing.

6. The method according to claim 1, wherein the puree is frozen for at least 24 hours before the step of thawing.

7. The method according to claim 1, wherein the puree is frozen for at least 72 hours before the step of thawing.

8. The method according to claim 1, wherein viscosity is measured using a consistometer.

9. A method for predicting yield loss of a tomato paste said method comprising the steps of:

freezing a tomato puree at about −8° C.;

thawing said tomato puree;

measuring viscosity of thawed tomato puree; and comparing the viscosity of said thawed tomato puree with viscosity of original tomato puree, thereby predicting the yield loss of the tomato paste.

10. The method according to claim 9, wherein the tomato puree is frozen for at least 48 hours before the step of thawing.

11. The method according to claim 9, wherein the tomato puree is frozen for at least 24 hours before the step of thawing.

12. The method according to claim 9, wherein the tomato puree is frozen for at least 72 hours before the step of thawing.

13. The method according to claim 9, wherein viscosity is measured using a consistometer.

* * * * *

UNITED STATES PATENT AND TRADEMARK OFFICE
CERTIFICATE OF CORRECTION

PATENT NO.         : 6,844,016 B2
APPLICATION NO.    : 10/641775
DATED              : January 18, 2005
INVENTOR(S)        : David Reid It is certified that error appears in the above-identified patent and that said Letters Patent is hereby corrected as shown below:

Drawings sheets 1 to 23 are to be replaced with the attached 23 sheets of drawings, showing amended Figures 1 though 21.

Signed and Sealed this
Fifteenth Day of March, 2011

David J. Kappos
*Director of the United States Patent and Trademark Office*

*Figure 1*

| Variety ID | Apparent viscosity at 50s⁻¹, (mPa.s) | | | | Apparent viscosity at 100s⁻¹, (mPa.s) | | | |
|---|---|---|---|---|---|---|---|---|
| | Control Juice | 30° Brix Paste | -5°C Frozen Juice | -8°C Frozen Juice | Control Juice | 30° Brix Paste | -5°C Frozen Juice | -8°C Frozen Juice |
| 15 | 190 | 50.6 | 93.7 | 98.4 | 130.8 | 32.5 | 57.5 | 65.4 |
| 30 | 374.7 | 82.5 | 130.4 | 137.5 | 247.0 | 50.4 | 81.6 | 89.0 |
| 31 | 232.7 | 47.1 | 133.3 | 131.5 | 157.2 | 32.5 | 84.2 | 88.2 |
| 34 | 198.8 | 23.3 | 69.6 | 94.7 | 134.7 | 15.9 | 45.9 | 66.0 |

| Variety ID | Apparent viscosity at 50s$^{-1}$, (mPa.s) | | | | Apparent viscosity at 100$^{-1}$, (mPa.s) | | | |
|---|---|---|---|---|---|---|---|---|
| | Control Juice[a] | 30° Brix Paste[a] | -5°C Frozen Juice[b] | -8°C Frozen Juice[b] | Control Juice[a] | 30° Brix Paste[a] | -5°C Frozen Juice[b] | -8°C Frozen Juice[b] |
| 15 | 190 ± 14 | 51 ± 8 | 94 ± 13 | 98 ± 10 | 131 ± 6 | 33 ± 4 | 58 ± 9 | 65 ± 6 |
| 30 | 375 ± 18 | 83 ± 31 | 130 ± 14 | 138 ± 12 | 247 ± 11 | 50 ± 17 | 82 ± 7 | 89 ± 6 |
| 31 | 233 ± 27 | 47 ± 7 | 133 ± 24 | 132 ± 13 | 157 ± 16 | 33 ± 4 | 84 ± 16 | 88 ± 12 |
| 34 | 199 ± 6.4 | 23 ± 2 | 70 ± 14 | 95 ± 11 | 135 ± 5 | 16 ± 2 | 46 ± 2 | 66 ± 8 |

[a] Mean ± standard deviation; n = 4
[b] Mean ± standard deviation; n = 12

*Figure 8*

| Variety ID | Apparent viscosity at 50s-1, (mPa.s) | | | | Apparent viscosity at 100-1, (mPa.s) | | | |
|---|---|---|---|---|---|---|---|---|
| | -5°C Frozen Juice | | -8°C Frozen Juice | | 5°C Frozen Juice | | -8°C Frozen Juice | |
| | (1 month) | (6 months) | (1 month) | (6 months) | (1 month) | (6 months) | (1 month) | (6 months) |
| 15 | 93.7 | 96.6 | 98.4 | 96.3 | 57.5 | 59.6 | 65.4 | 60.6 |
| 30 | 130.4 | 128.5 | 137.5 | 141.5 | 81.6 | 81.4 | 89.0 | 89.8 |
| 31 | 133.3 | 126.7 | 131.5 | 130.5 | 84.2 | 77.0 | 88.2 | 81.8 |
| 34 | 69.6 | 69.8 | 94.7 | 91.4 | 45.9 | 45.8 | 66.0 | 61.3 |

*Figure 9*

| Variety ID | Apparent viscosity at 50s-1, (mPa.s) | | | | Apparent viscosity at 100-1, (mPa.s) | | | |
|---|---|---|---|---|---|---|---|---|
| | Control Juice | 30° Brix Paste | -5°C Frozen Juice | -8°C Frozen Juice | Control Juice | 30° Brix Paste | -5°C Frozen Juice | -8°C Frozen Juice |
| 5557 | 200.1 | 84.9 | 122.4 | 175.9 | 133.3 | 51.2 | 83.4 | 123.1 |
| 5558 | 169.5 | 101.3 | 157.2 | 157.4 | 108.3 | 63.8 | 103.3 | 104.7 |
| 5559 | 190.0 | 101.7 | 130.3 | 150.1 | 129.5 | 61.2 | 87.4 | 99.6 |
| 5560 | 309.1 | 151.6 | 196.5 | 218.3 | 207.2 | 100.2 | 126.5 | 146.8 |
| 5561 | 199.5 | 91.5 | 123.4 | 140.8 | 136.9 | 53.3 | 84.5 | 95.9 |
| 5562 | 248.2 | 145.0 | 171.6 | 177.2 | 169.4 | 88.6 | 114.2 | 116.9 |
| 5563 | 155.7 | 77.2 | 127.3 | 131.6 | 110.1 | 51.0 | 87.5 | 90.1 |
| 5564 | 138.5 | 70.1 | 73.0 | 77.4 | 103.1 | 50.4 | 54.2 | 56.0 |
| 5565 | 227.8 | 96.8 | 146.9 | 208.1 | 153.0 | 61.6 | 95.6 | 132.7 |
| 5566 | 321.8 | 108.6 | 252.2 | 282.5 | 217.6 | 63.6 | 164.2 | 189.0 |
| 5567 | 330.5 | 119.2 | 153.1 | 185.6 | 226.2 | 79.6 | 103.5 | 129.7 |
| 5568 | 137.0 | 77.2 | 86.0 | 92.4 | 94.7 | 53.2 | 58.1 | 62.7 |
| 5569 | 322.7 | 136.4 | 185.4 | 202.3 | 219.6 | 93.7 | 122.8 | 137.7 |

*Figure 14A*

| Variety ID | Apparent viscosity at 50s-1, (mPa.s) | | | | Apparent viscosity at 100-1, (mPa.s) | | | |
|---|---|---|---|---|---|---|---|---|
| | Control Juice | 30° Brix Paste | -5°C Frozen Juice | -8°C Frozen Juice | Control Juice | 30° Brix Paste | -5°C Frozen Juice | -8°C Frozen Juice |
| 5570 | 258.7 | 114.4 | 139.6 | 193.6 | 173.1 | 72.1 | 83.4 | 126.5 |
| 5571 | 125.4 | 55.9 | 69.2 | 73.6 | 81.6 | 36.2 | 45.7 | 47.0 |
| 5572 | 83.8 | 37.1 | 44.0 | 50.5 | 49.1 | 27.3 | 26.9 | 31.1 |
| 5573 | 294.0 | 114.6 | 216.4 | 223.0 | 197.5 | 66.5 | 140.5 | 139.6 |
| 5574 | 208.7 | 62.5 | 108.6 | 129.1 | 148.9 | 39.4 | 75.6 | 89.5 |
| 5575 | 214.0 | 148.8 | 159.4 | 161.0 | 138.6 | 86.9 | 101.4 | 102.7 |
| 5577 | 223.8 | 126.2 | 142.5 | 176.6 | 145.7 | 78.8 | 88.9 | 109.0 |
| 5578 | 231.7 | 162.7 | 171.3 | 188.6 | 157.3 | 104.5 | 113.1 | 123.2 |
| 5579 | 299.5 | 161.2 | 173.3 | 173.0 | 205.5 | 103.4 | 120.6 | 115.1 |
| 5580 | 179.2 | 79.8 | 90.8 | 92.8 | 122.7 | 52.2 | 60.0 | 63.3 |
| 5581 | 302.0 | 120.2 | 171.2 | 194.1 | 207.3 | 75.4 | 115.9 | 125.9 |
| 5582 | 242.1 | 111.6 | 154.4 | 173.2 | 166.5 | 66.4 | 101.2 | 107.5 |

Figure 14B

| Variety ID | Apparent viscosity Loss at 50s⁻¹, (mPa.s) | | | Apparent viscosity Loss at 100 s⁻¹, (mPa.s) | | |
|---|---|---|---|---|---|---|
| | 30° Brix Paste | -5°C Frozen Juice | -8°C Frozen Juice | 30° Brix Paste | -5°C Frozen Juice | -8°C Frozen Juice |
| 5557 | 115.2 | 117.7 | 80.5 | 82.0 | 78.4 | 49.8 |
| 5558 | 68.2 | 50.1 | 67.0 | 44.5 | 32.6 | 43.7 |
| 5559 | 88.3 | 99.1 | 96.1 | 68.3 | 70.4 | 70.0 |
| 5560 | 157.5 | 148.5 | 147.2 | 106.9 | 107.2 | 99.4 |
| 5561 | 108.0 | 115.9 | 115.0 | 83.7 | 80.8 | 81.2 |
| 5562 | 103.2 | 113.8 | 127.3 | 80.8 | 82.3 | 92.2 |
| 5563 | 78.5 | 68.0 | 80.3 | 59.1 | 50.8 | 60.3 |
| 5564 | 68.4 | 108.1 | 117.2 | 52.7 | 78.6 | 88.3 |
| 5565 | 131.0 | 119.5 | 76.0 | 91.4 | 85.3 | 59.6 |
| 5566 | 213.3 | 102.6 | 95.8 | 153.9 | 78.2 | 66.6 |
| 5567 | 211.3 | 215.7 | 201.1 | 146.6 | 150.3 | 135.9 |
| 5568 | 59.7 | 92.8 | 100.7 | 41.5 | 66.2 | 73.0 |
| 5569 | 186.3 | 173.8 | 176.7 | 125.9 | 123.4 | 121.1 |

Figure 15A

| Variety ID | Apparent viscosity Loss at 50s⁻¹, (mPa.s) | | | Apparent viscosity Loss at 100 s⁻¹, (mPa.s) | | |
|---|---|---|---|---|---|---|
| | 30° Brix Paste | -5°C Frozen Juice | -8°C Frozen Juice | 30° Brix Paste | -5°C Frozen Juice | -8°C Frozen Juice |
| 5570 | 144.3 | 158.0 | 121.4 | 101.0 | 118.1 | 86.1 |
| 5571 | 69.6 | 98.9 | 108.0 | 45.4 | 66.1 | 76.1 |
| 5572 | 46.7 | 83.8 | 89.3 | 21.8 | 53.2 | 59.7 |
| 5573 | 179.4 | 112.5 | 127.3 | 131.0 | 82.9 | 97.1 |
| 5574 | 146.2 | 140.7 | 135.7 | 109.5 | 102.1 | 99.9 |
| 5575 | 65.2 | 92.5 | 109.2 | 51.7 | 64.8 | 75.9 |
| 5577 | 97.6 | 120.1 | 103.5 | 66.9 | 85.0 | 76.6 |
| 5578 | 69.0 | 97.6 | 99.3 | 52.8 | 71.3 | 73.7 |
| 5579 | 138.3 | 163.2 | 182.4 | 102.1 | 111.7 | 130.2 |
| 5580 | 99.5 | 130.0 | 142.5 | 70.4 | 92.1 | 100.4 |
| 5581 | 181.9 | 168.1 | 164.2 | 131.9 | 118.4 | 120.9 |
| 5582 | 130.4 | 125.9 | 125.1 | 100.1 | 92.9 | 98.9 |

Figure 15B